(12) United States Patent
Leung et al.

(10) Patent No.: US 8,389,242 B2
(45) Date of Patent: *Mar. 5, 2013

(54) PROCESS FOR PRODUCING APO2L

(75) Inventors: Woon-Lam Susan Leung, San Mateo, CA (US); James R. Swartz, Menlo Park, CA (US)

(73) Assignee: Genentech, Inc., South San Francisco, CA (US)

( * ) Notice: Subject to any disclaimer, the term of this patent is extended or adjusted under 35 U.S.C. 154(b) by 225 days.

This patent is subject to a terminal disclaimer.

(21) Appl. No.: 12/586,023

(22) Filed: Sep. 16, 2009

(65) Prior Publication Data

US 2011/0059484 A1    Mar. 10, 2011

Related U.S. Application Data

(63) Continuation of application No. 11/536,551, filed on Sep. 28, 2006, now abandoned, which is a continuation of application No. 11/077,272, filed on Mar. 10, 2005, now Pat. No. 7,294,483.

(60) Provisional application No. 60/552,678, filed on Mar. 11, 2004.

(51) Int. Cl.
*C12N 15/09* (2006.01)
*C12P 21/02* (2006.01)
*C12P 1/04* (2006.01)
*C07K 14/52* (2006.01)

(52) U.S. Cl. ....... 435/69.4; 435/69.1; 435/170; 530/399

(58) Field of Classification Search .................. 435/69.4, 435/69.1, 170; 530/399
See application file for complete search history.

(56) References Cited

U.S. PATENT DOCUMENTS

| | | | |
|---|---|---|---|
| 5,304,472 A | 4/1994 | Bass et al. | |
| 5,342,763 A | 8/1994 | Swartz | |
| 6,251,626 B1 | 6/2001 | Stougaard et al. | |
| 6,337,191 B1 | 1/2002 | Swartz et al. | |
| 6,559,122 B1 | 5/2003 | Oeswein et al. | |
| 7,294,483 B2 | 11/2007 | Leung et al. | |
| 2003/0124664 A1 | 7/2003 | Joly | |
| 2004/0146896 A1* | 7/2004 | Rong et al. ........................ 435/6 |

FOREIGN PATENT DOCUMENTS

| | | |
|---|---|---|
| WO | 97/01633 | 1/1997 |
| WO | 97/25428 | 7/1997 |
| WO | WO 99/00423 | 1/1999 |
| WO | WO 00/55353 | 9/2000 |
| WO | 01/00832 A1 | 1/2001 |
| WO | WO 02/40497 A | 5/2002 |

OTHER PUBLICATIONS

Argast et al., "A second transport system for sn- glycerol-3-phosphate in *Escherichia coli*" *J. Bacteriol.* 136:1070-1083 (1978).

Ashkenazi et al., "Apoptosis regualtion by death and decoy receptors" *FASEB journal* 13:A1336 (Apr. 23, 1999).

Ashkenazi et al., "Targeting death and decoy receptors of the tumour-necrosis factor superfamily" *Nature Reviews—cancer* 2:420-430 (2002).

(Continued)

*Primary Examiner* — Rosanne Kosson
(74) *Attorney, Agent, or Firm* — Diane L. Marschang

(57) ABSTRACT

A process is described for producing a polypeptide heterologous to *E. coli* wherein *E. coli* cells comprising nucleic acid encoding the polypeptide are cultured in a culture medium while feeding to the culture medium a transportable organophosphate, such that the nucleic acid is expressed. The polypeptide is then recovered from the cells.

24 Claims, 6 Drawing Sheets

OTHER PUBLICATIONS

Bachmann., "Derivations and Genotypes of Some Mutant Derivatives of *Escherichia coli* K-2." *Escherichia coli and Salmonella Typhimurium: Cellular and Molecular Biology*. (Washington, DC: American Society for Microbiology.), Chapter 72, 2:1190-1219 (1987).

Brzoska et al., "ugp-dependent transport system for sn-glycerol 3-phosphate of *Escherichia coli*" *Phosphate Metabolism and Cellular Regulation in Microorganisms*, A. Torriani-Gorini, F.G. Rothman, S. Silver, A. Wr, Washington, D.C. : American Society for Microbiology pp. 170-177.

Brzoska, P. et al., "The pho regulon-dependent ugp uptake system for glycerol-3-phosphate in *Escherichia coli* is trans inhibited by $P_i$" *J. Bacteriol*. 176:15-20 (1994).

Chang et al., "High-Level Secretion of Human Growth Hormone by *Escherichia coli*" *Gene* 55:189-196 (1987).

Elashvili et al., "phnE and glpT genes enhance utilization of organophosphates in *Escherichia coli* K-12" *Appl. Environ. Microbiol*. 64:2601-2608 (1998).

Elvin et al., "$P_i$ exchange mediated by the glpT-dependent sn-glycerol-3-phosphate transport system in *Escherichia coli*" *J. Bacteriol*. 161:1054-1058 (1985).

Garcia et al., "The *E. coli* dnaY Gene Encodes an Arginine Transfer RNA." *Cell*. 45:453-459 (1986).

Jewett et al., "Prokaryotic systems for in vitro expression" *Gene Cloning and Expression Technologies*, Weiner et al., Westborough, Mass.:Eaton Publishing Co. pp. 391-411 (2002).

Kasahara et al., "Dual regulation of the ugp operon by phosphate and carbon starvaion at two interspaced promoters" *J. Bacteriol*. 173:549-558 (1991).

Kim et al., "Regeneration of adenosine triphosphate from glycolytic intermediates for cell-free protein synthesis" *Biotechnol Bioeng*. 74(4):309-316 (Aug. 20, 2001).

Komine et al., "Genomic Organization and Physical Mapping of the Transfer RNA Genes in *Escherichia coli* K12" *J. Mol. Biol*. 212:579-598 (1990).

Kunkel et al., "Rapid and efficient site-specific mutagenesis without phenotypic selection" *Methods Enzymol*. 154:367-382 (1987).

Lin, E.C.C., "Dissimilatory Pathways for sugars, polyols and carboxylates" *Escherichia coli and Salmonella, Cellular and Molecular Biol.*, 2d edition, Washington, D.C.:ASM Press, Chapter 20, vol. 1:307-342, 1996.

Lin, E.C.C., "Glycerol dissimilation and its regulation in bacteria" *Annu. Rev. Microbiol*. 30:535-578 (1976).

Patnaik et al., "*E. coli*-based in vitro transcription/translation: in vivo-specific synthesis rates and high yields in a batch system" *Biotechniques* 24(5) :862-865 (May 1998).

Pitti et al., "Induction of Apoptosis by Apo-2 Ligand, a New Member of the Tumor Necrosis Factor Cytokine Family" *Journal of Biological Chemistry* 271:12687-12690 (1996).

Pluckthun, A., "Mono- and bivalent antibody fragments produced in *Escherichia coli* : engineering, folding and antigen binding" *Immunol Rev*. 130:151-188 (1992).

Rosenberg, "Phosphate transport in prokaryotes" *Ion Transport in Prokaryotes*, B. P. Rosen and S. Silver, New York:Academic Press, Inc. pp. 205-248 (1987).

Scholtissek and Grosse, "A Cloning Cartridge of λ $t_o$ Terminator" *Nucl. Acids Res*. 15(7) :3185 (1987).

Schweizer and Boos, "Characterization of the ugp region containing the genes for the phoB dependent sn-glycerol-3-phosphate transport system of *Escherichia coli*" *Mol. and Gen. Genetics* 197:161-168 (1984).

Schweizer, H. et al., "Characteristics of a binding protein-dependent transport system for sn-glycerol-3-phosphate in *Escherichia coli* that is part of the pho regulon" *J. Bacteriol*. 150:1154-1163 (1982).

Schweizer, H. et al., "Mapping of two ugp genes coding for the pho regulon-dependent sn-glycerol-3-phosphate transport system of *Escherichia coli*" *J. Bacteriol*. 150:1164-1171 (1982).

Schweizer, H. et al., "Regulation of ugp, the sn-glycerol-3-phosphate transport system of *Escherichia coli* K-12 that is part of the pho regulon" *J. Bacteriol*. 163:392-394 (1985).

Sidhu, S. et al., "High copy display of large proteins on phage for functional selections" *J. Mol. Biol*. 296(2):487-495 (2000).

Silhavy, T. J. et al., "Periplasmic protein related to the sn-glycerol-3-phosphate *Escherichia coli*" *J. Bacteriol*. 126:951-958 (1976).

Skerra, "Bacterial expression of immunoglobulin fragments" *Curr. Opin. Immunol*. 5:256-262 (1993).

Slanier, Adelberg and Ingraham, "The methods of microbiology" *The Microbial World*, 4th edition, NJ:Prentice Hall, Chapter 2, pp. 28-29 (1976).

Spinelli, S. et al., "The crystal structure of a llama heavy chain variable domain" *Nat. Struct. Biol*. 3(9):752-757 (1996).

St. John and Goldberg, "Effects of starvation for potassium and other inorganic ions on protein degradation and ribonucleic acid synthesis in *Escherichia coli*" *J. Bacteriol*. 143(3):1223-1233 (1980).

Su, Ti-Zhi et al., "Carbon-starvation induction of the ugp operon, encoding the binding protein-dependent sn-glycerol-3-phosphate transport system in *Escherichia coli*" *Mol. Gen. Genet*. 230:28-32 (1991).

Sutcliffe, J., "Complete Nucleotide Sequence of the *Escherichia coli* Plasmid pBR322" *Cold Spring Harbor Symposia on Quantitative Biology* 43:77-90 (1979).

Vergeles, J. et al., "High efficiency of glycerol 2-phosphate and sn-glycerol 3-phosphate as nucleotidyl acceptors in snake venom phosphodiesterase esterifications" *European Journal of Biochemistry* 233:442-447 (1995).

Wanner, "Phosphorus Assimilation and Control of the Phosphate Regulon" *Escherichia coli and Salmonilla Cellular Mol. Biol.*, Neidhardt, 2d edition, American Society for Microbiology Press pp. 1357-1365 (1996).

Wiley et al., "Identification and Characterization of a New Member of the TNF Family that Induces Apoptosis" *Immunity* 3:673-682 (1995).

Xavier, K. et al., "Kinetic analysis by in vivo $^{31}P$ nuclear magnetic resonance of internal $P_i$ during the uptake of sn-glycerol-3-phosphate by the pho regulon-dependent ugp system and the glp regulon-depended glpT system" *J. Bacteriol*. 177:699-704 (1995).

* cited by examiner

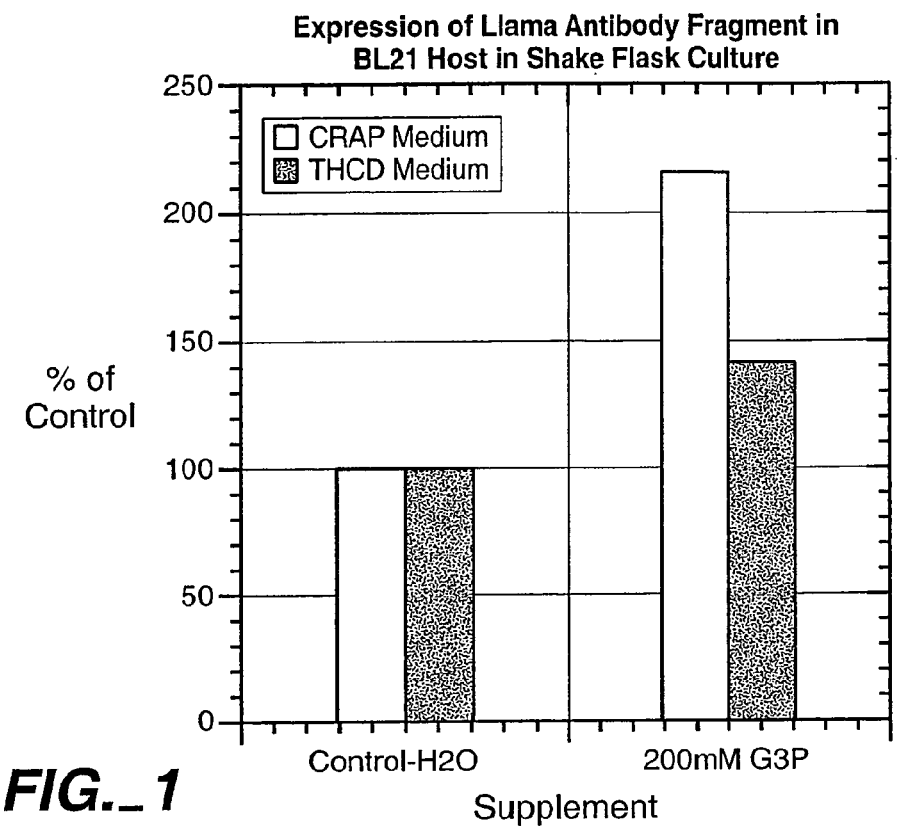
FIG._1
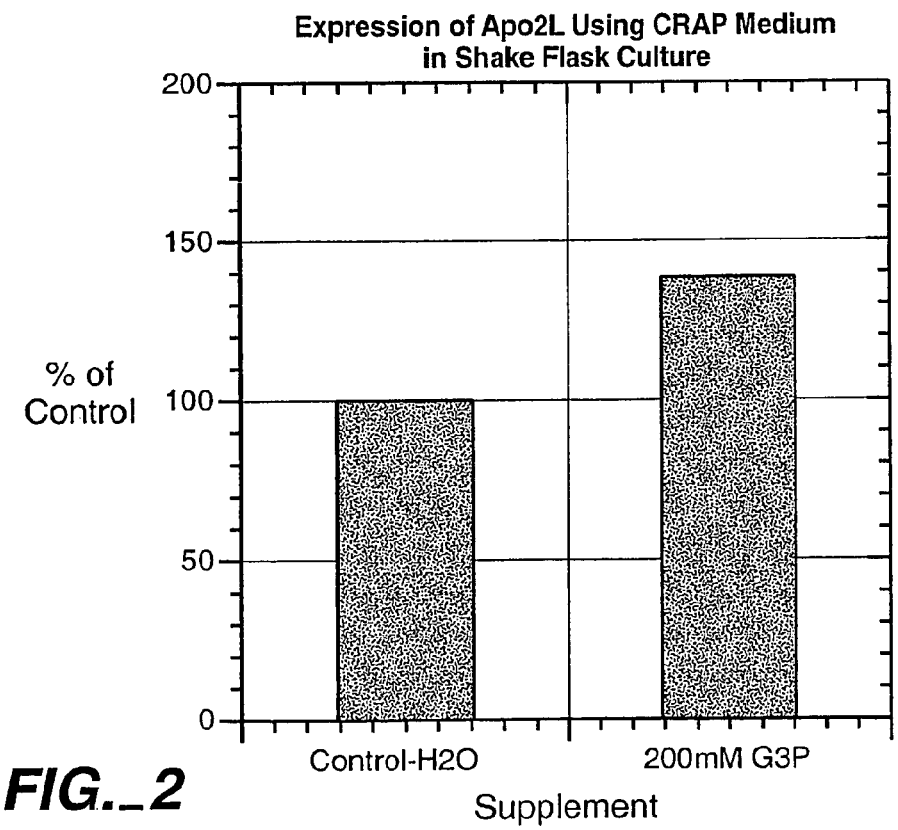
FIG._2

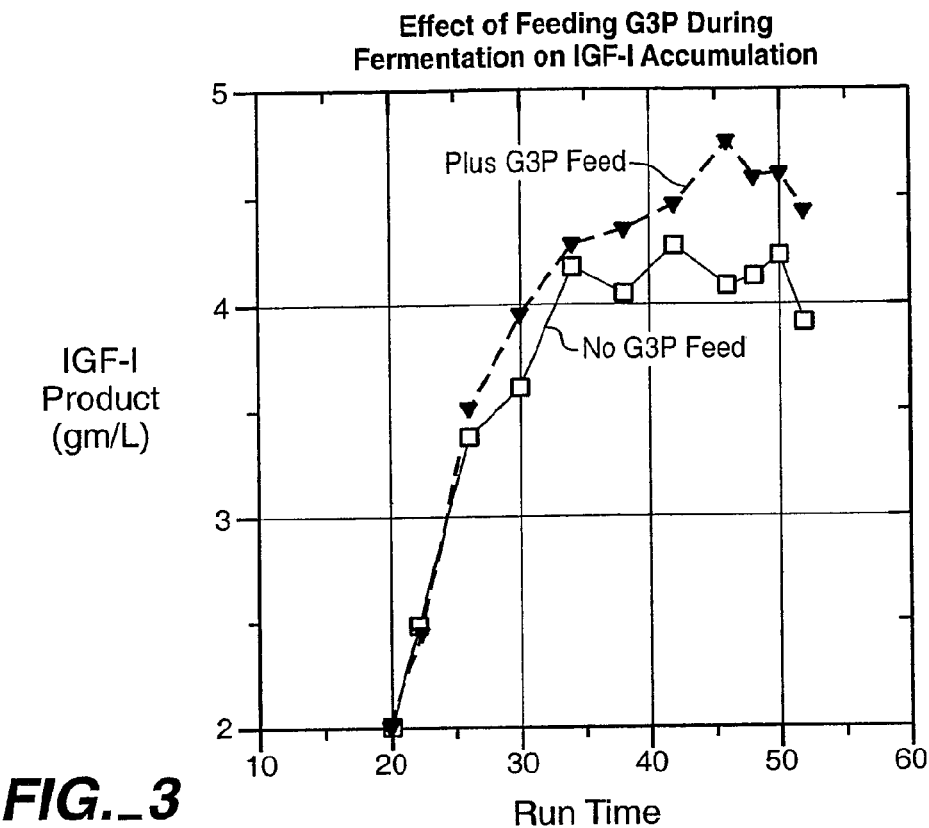
FIG._3
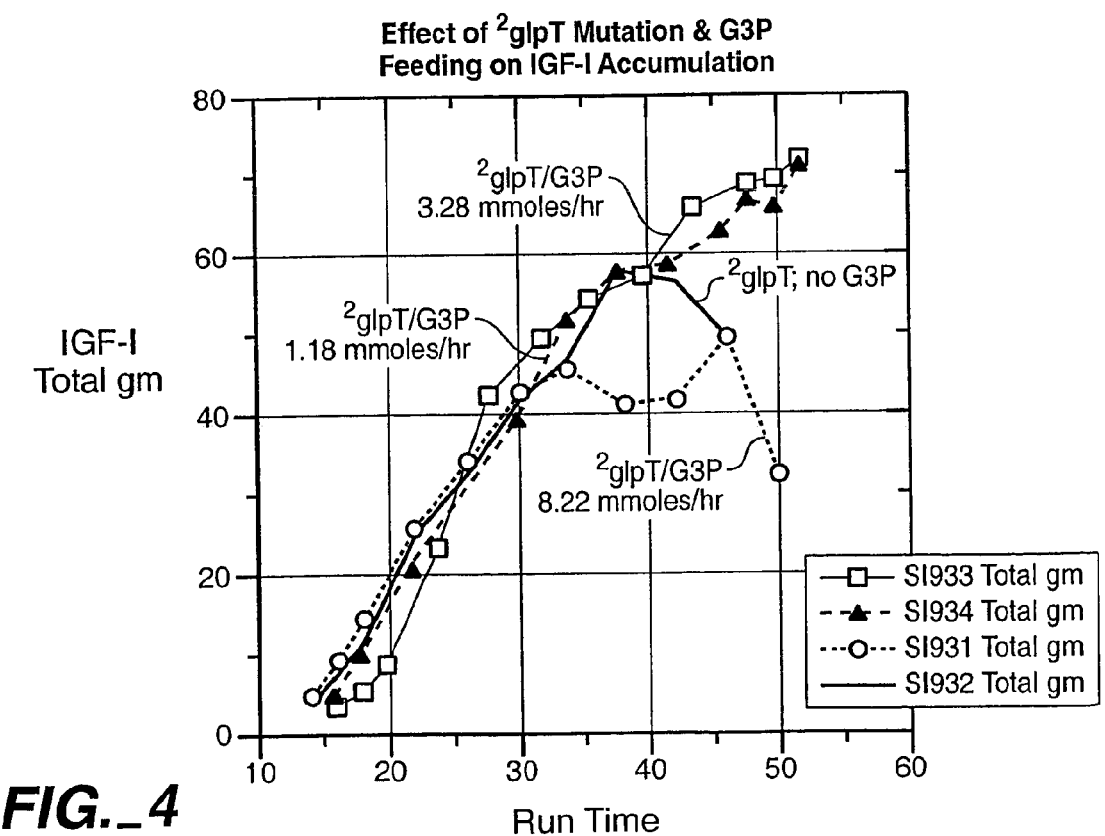
FIG._4

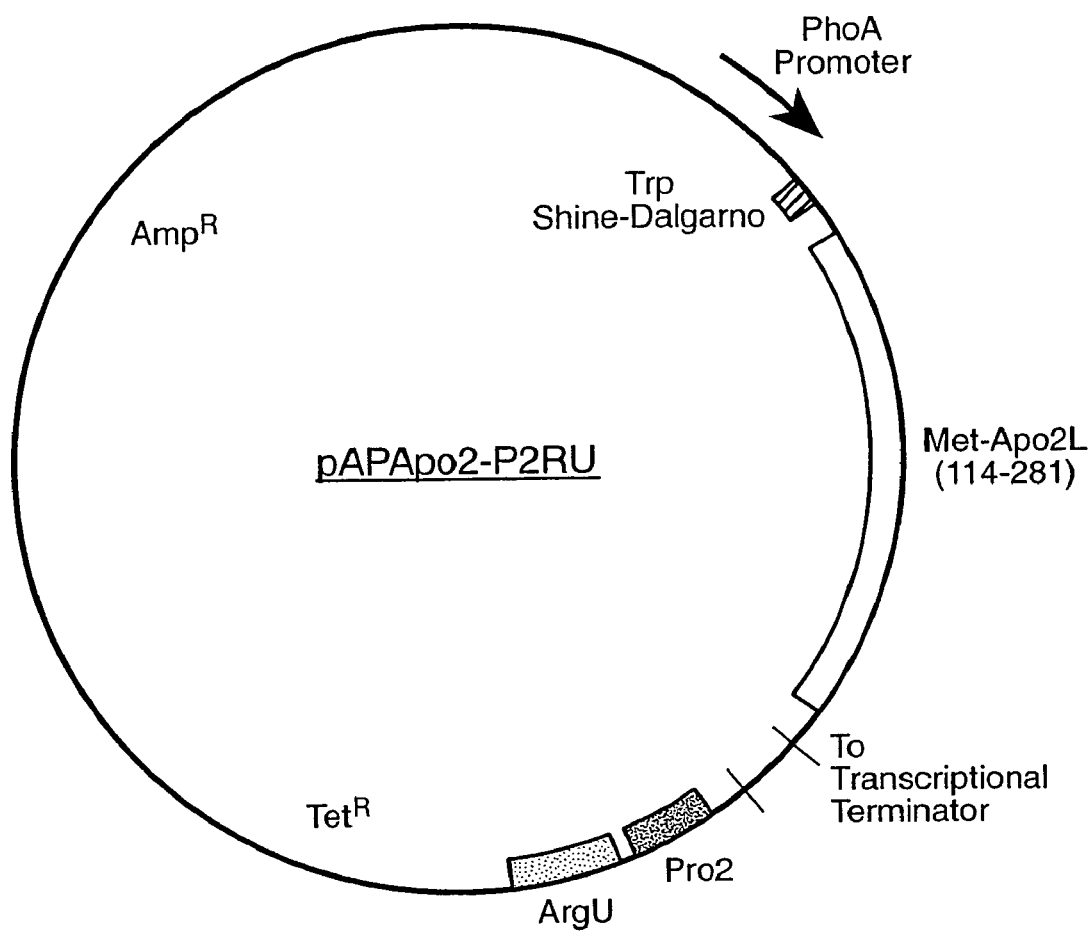
FIG._5

```
  1 TTTCCTCACTGACTATAAAGAATAGAGAAGGAAGGGCTTCAGTGACCGGCTGCCTGGCTGACTTACAGCAGTCAGACTCTGACAGGATC

1 ATGGCTATGATGGAGGTCCAGGGGGACCCAGCCTGGGACAGACCTGCTGCTGTGATCTTCACAGTGCTCCTGCAGTCTCTCTGT
  1 MetAlaMetMetGluValGlnGlyProSerLeuGlyGlyProSerLeuGlnThrCysValLeuIleValIlePheThrValLeuLeuGlnSerLeuCys

181 GTGGCTGTAACTTACGTGTACTTACCAACGAGATGCAGGACAAGTACTCCAAAAGTGCATTGCTTGTTTCTTAAAGAA
 31 ValAlaValThrTyrValTyrPheThrAsnThrTyrPheAsnLysTyrSerLysIleAlaCysPheLeuLysGlu

271 GATGACAGTTATTGGACCCCAATGACGAGAGACAGAGATGAACAGCCCCTGCAAGTCAAGTGGCAACTCCGTCAGCTCGTAGAAAG
 61 AspAspSerTyrTrpAspProAsnAspGluGluArgAspGluGlnProLeuGlnValLysTrpGlnLeuArgGlnLeuValArgLys

361 ATGATTTGAAACCTCTGAGAACCATTTCTACAGTTCAAGAAAGCAACACATTTCTCCCCTAGTGAGAGAAAGAGGTCCNCAG
 91 MetIleLeuArgThrSerGluThrIleSerThrValGlnGluLysGlnAsnIleSerProLeuValArgGluArgGlyProGln

451 AGAGTAGCAGCTCACATAACTGGGAACCAGAAGCAACACATTGTCTTCTCCAAACTCCAAGAATGAAAAGGCTCTGGGCCGCAAA
121 ArgValAlaAlaHisIleThrGlyThrArgGlyThrArgSerAsnThrLeuSerSerProAsnSerLysAsnGluLysAlaLeuGlyArgLys

541 ATAAACTCCTGGGAATCATCAAGGAGTGGGCATTCATTCCTGAGCAACTTGCACTTGAGGAATGGTGAACTGTCATCCATGAAAAAAGG
151 IleAsnSerTrpGluSerSerArgSerGlyHisSerPheLeuSerAsnLeuHisLeuArgAsnGlyGluLeuValIleHisGlyLysGly

631 TTTTACTACTAAGTATCCTGACCTATATTGTTGATGAAAAGTGCTAGAAATGCAGAATATGGACTCTAT
181 PheTyrTyrIleTyrSerGlnThrTyrPheArgPheGlnGluGlyIleLeuLysGluAsnAspLysGlnMetValGlnTyrIle

721 TACAAAATACACAAGTATCCTGACCTATATTGTTGATGAAAAGTGCTAGAAATGCAGAATATGGACTCTAT
211 TyrLysTyrThrSerTyrProAspProIleLeuLeuMetLysSerAlaArgAsnSerCysTrpSerLysAspAlaGluTyrGlyLeuTyr

811 TCCATCTATCAAGGGGAATATTTGAGCTTAAGGAAAATGACAGAATTTTTGTTTCTGTAACAAATGACACTTGATAGACATGGACCAT
241 SerIleTyrGlnGlyGlyIleLeuPheGluLeuLysLysAsnAspArgIlePheValSerValThrAsnGluHisLeuIleAspMetAspHis

901 GAAGCCAGTTTTTTCGGGGCCTTTTAGTTGGCTAACTGACCTGGAAAGAAAAAGCAATAACCTCAAAGTGACTATTCAGTTTTCAGGAT
271 GluAlaSerPhePheGlyAlaPheLeuValGlyStp

991 GATACACTATGAAGATGTTTCAAAAAATCTGACCAAAACAAAACAGAAA
```

FIG._6

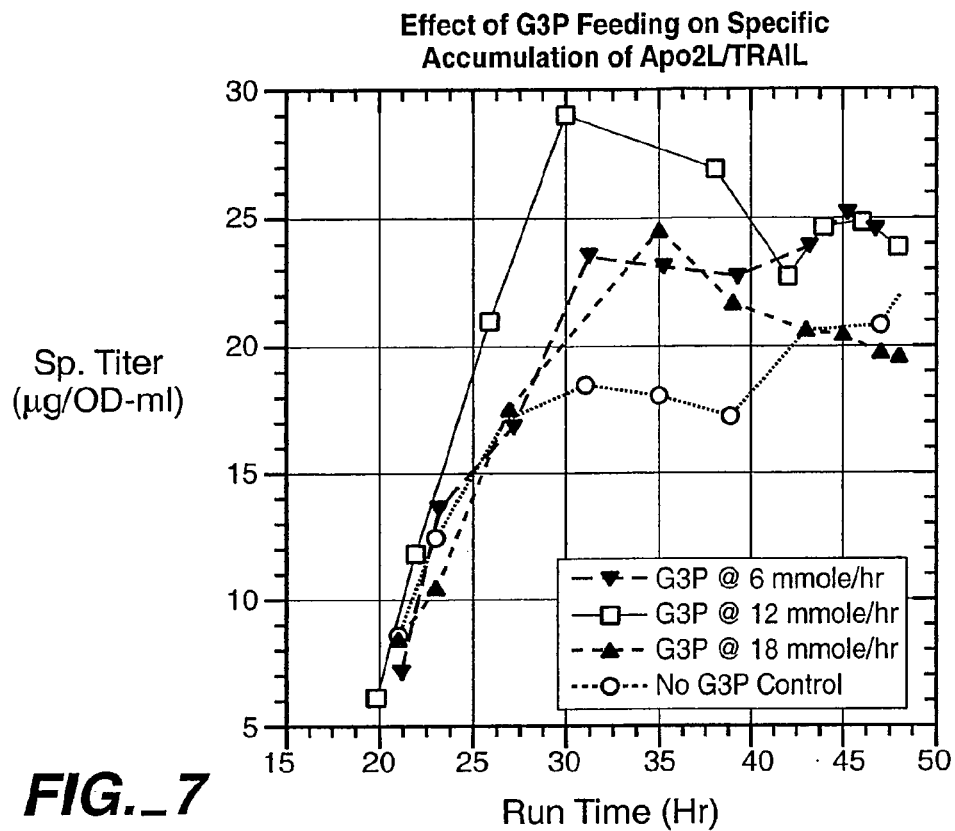
FIG._7
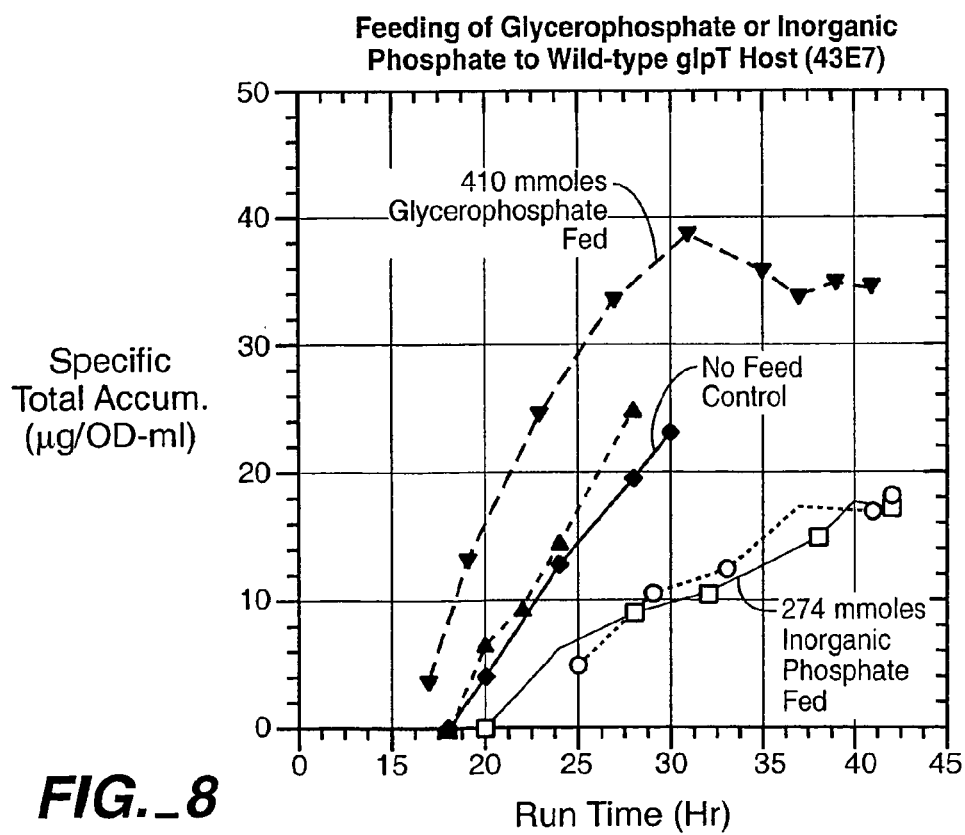
FIG._8

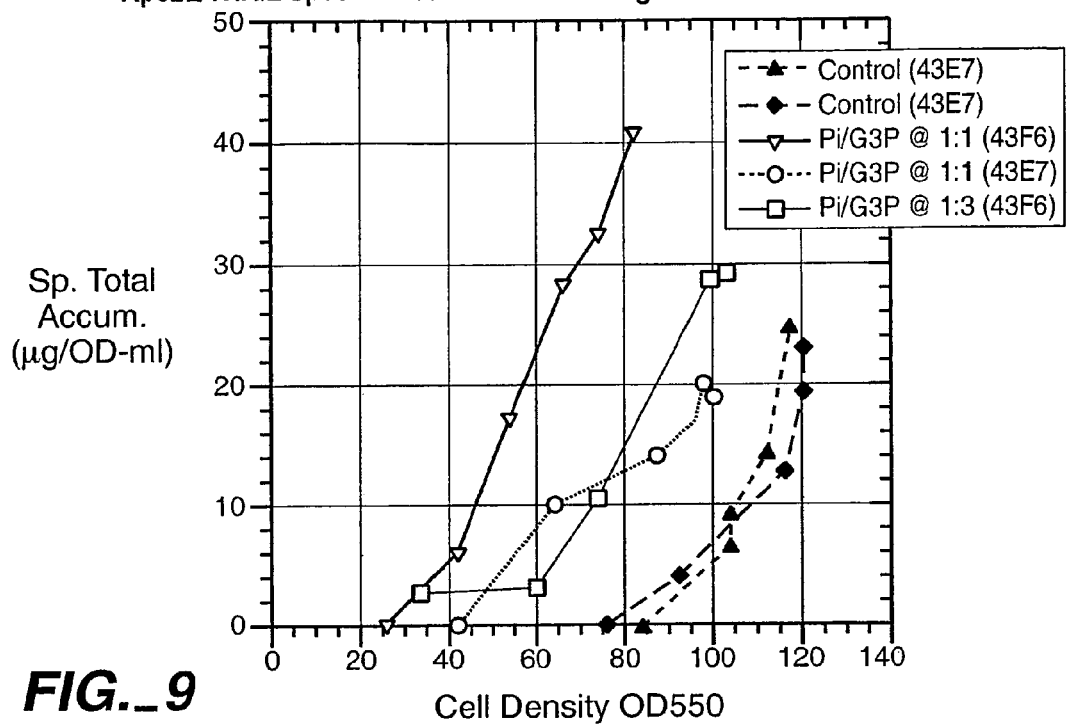
FIG._9
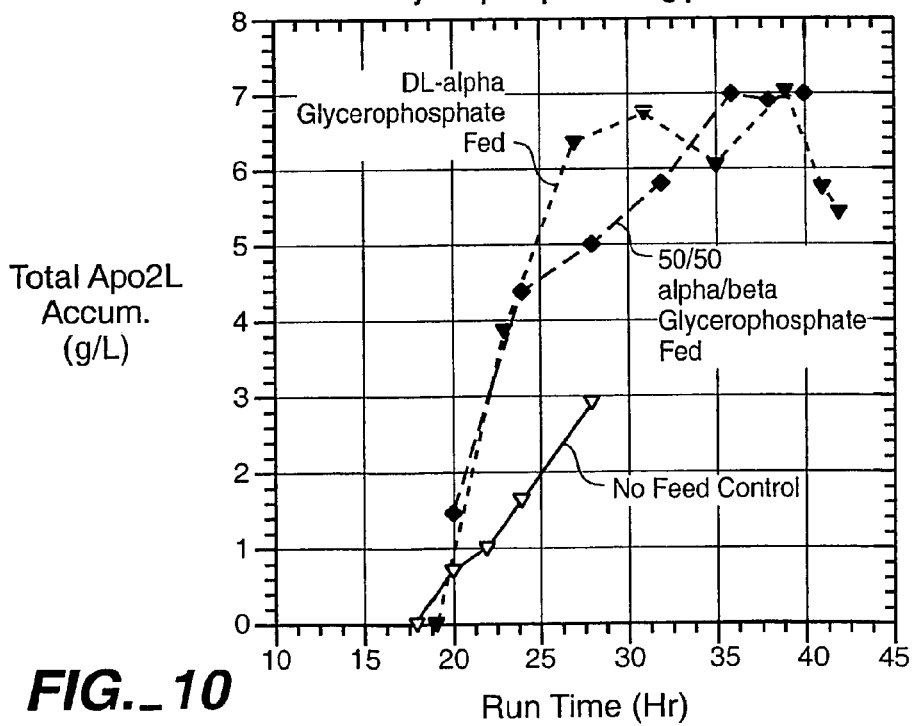
FIG._10

PROCESS FOR PRODUCING APO2L

RELATED APPLICATIONS

This application is a continuation application of application Ser. No. 11/536,551, filed Sep. 28, 2006, now abandoned, which is a continuation application of application Ser. No. 11/077,272, filed Mar. 10, 2005, now issued as U.S. Pat. No. 7,294,483 B2 on Nov. 13, 2007, which claims benefit of application No. 60/552,678 filed Mar. 11, 2004, the entire contents of which are incorporated herein by reference.

BACKGROUND OF THE INVENTION

1. Field of the Invention

The invention relates to a process for producing a polypeptide heterologous to *E. coli*. More particularly, the invention is directed to using organophosphate to improve yield of such polypeptides.

2. Description of Related Art

Expression of heterologous proteins by *Escherichia coli*, aided by the well-understood molecular biology and relative ease in genetic manipulation of the microorganism, has been very productive in both laboratory and industry. Typically, an inducible promoter (for example, the alkaline phosphatase promoter, the tac promoter, the arabinose promoter, etc.) is employed for the regulation of heterologous protein expression. The requirement of an induction event provides the researcher the opportunity to manage the timing of expression of the target protein. This ability is especially important for those heterologous proteins that are not well tolerated at high concentrations by the host. By achieving desirable cell density prior to the induction of expression, the volumetric yield of the desired protein may be maximized.

Cells cease to grow when the microorganism is deprived of a required nutrient. The limiting component may be carbon, nitrogen, phosphate, oxygen or any of the elements required by the cell. Under such conditions, the cells exit from the growth phase. A way to alleviate the culture of the stress responses caused by the nutrient limitation is to provide a feed of the lacking component. Common feeds introduced into fed-batch fermentation processes include glucose, amino acids, oxygen, etc.

In the case of cellular phosphorus (P), the requirement for phosphate supply is not surprising given that P is the fifth most abundant element in a cell behind carbon, oxygen, nitrogen, and hydrogen. Slanier, Adelberg and Ingraham, *The Microbial World*, 4$^{th}$ ed. (Prentice Hall, NJ 1976), p. 1357. Phosphorus is an essential component in numerous macromolecules such as nucleic acids, liposaccharides and membrane lipids. Furthermore, its role in the high-energy phosphoanhydride bonds makes it especially important in energy metabolism. *E. coli* is capable of utilizing inorganic phosphate (Pi), organophosphate or phosphonate as the primary P source. The uptake of Pi from the environment can be achieved through two transporter systems, the Pit and the Pst systems. For the organophosphates, most are non-transportable and they first need to be hydrolyzed enzymatically in the periplasm before the released Pi can be taken up by the Pi transport system(s). Only a few organophosphates are transportable, and glycerol-3-phosphate (G3P) is one such example. G3P and glycerophosphate-1-phosphate (G1P) are known as alpha-glycerophosphates. In response to Pi-limitation and carbon-limitation, *E. coli* is capable of taking up available intact G3P from the external environment into the intracellular compartment, where G3P is metabolized to yield needed phosphate or carbon. Wanner, "Phosphorus Assimilation and Control of the Phosphate Regulon", in *Escherichia coli and Salmonella Cellular and Molecular Biology*, Neidhardt, ed., (second edition), American Society for Microbiology Press (1996), pp. 1357-1365.

Further references on G3P are Silhavy et al., *J. Bacteriol.*, 126: 951-958 (1976) on the periplasmic protein related to the sn-glycerol-3-phosphate transport system of *E. coli*; Argast et al., *J. Bacteriol.*, 136: 1070-1083 (1978) on a second transport system for sn-glycerol-3-phosphate in *E. coli*; Elvin et al., *J. Bacteriol.*, 161: 1054-1058 (1985) on Pi exchange mediated by the glpT-dependent G3P transport system; Rao et al., *J. Bacteriol.*, 175: 74-79 (1993) on the effect of glpT and glpD mutations on expression of the phoA gene in *E. coli*; and Elashvili et al., *Appl. Environ. Microbiol.*, 64: 2601-2608 (1998) on phnE and glpT genes enhancing utilization of organophosphates in *E. coli* K-12. Further, Vergeles et al., *Eur. J. Biochem.*, 233: 442-447 (1995) disclose the high efficiency of glycerol-2-phosphate (G2P), otherwise known as beta-glycerophosphate, and G3P as nucleotidyl acceptors in snake venom phosphodiesterase esterifications.

The current understanding of the two transport systems for the uptake of exogenous G3P in *E. coli*, the Ugp and GlpT transport systems, has been well summarized in the book *Escherichia coli and Salmonella, Cellular and Molecular Biology* edited by Neidhardt et. al. (second edition), supra, pp. 1364 referring to references 13 and 81. The Ugp operon belongs to the pho regulon. It is induced by phosphate limitation and positively regulated by phoB protein. The Ugp system is a periplasmic binding protein-dependent multi-component transport system, with ugpB encoding the periplasmic binding protein, ugpA and ugpC encoding integral membrane channel proteins, and ugpC encoding ATPase. GlpT is part of the glp system that mediates the uptake and metabolism of glycerol, G3P, and glycerol phosphoryl phosphodiesters (Lin et al., *Annu. Rev. Microbiol.*, 30: 535-578 (1976); Chapter 20; pg 307-342 Dissimilatory Pathways for sugars, polyols and carboxylates. *Escherichia coli* and *Salmonella*, Cellular and Molecular Biology, second edition). This transport system is an anion exchanger that is known to mediate the efflux of Pi from the cytoplasm by exchange with external G3P. In a wild-type strain growing on G3P, while little Pi is released by cells taking up G3P via the Ugp system, Pi can be released into the periplasm when G3P is taken up via the GlpT system. If a repressive amount of Pi is released as a result of glpT-permease-mediated efflux, the pho regulon activity, the Ugp system included, will be shut off. Under certain conditions, GlpT is the only route for the exit of Pi from the cell by exchange with external G3P. Elvin et al., *J. Bacteriol.*, 161: 1054-1058 (1985); Rosenberg, "Phosphate transport in prokaryotes," p. 205-248. In B. P. Rosen and S. Silver (ed.), *Ion Transport in Prokaryotes* (Academic Press, Inc., New York, 1987).

When the capacities of the Ugp and the GlpT systems are compared to transport G3P, the maximal velocities of the two systems are similar. The apparent affinity for G3P is higher with the Ugp system than with the GlpT system. Likely, both systems will be able to supply enough G3P for cell growth if available in the growth medium. However, G3P transported exclusively via the Ugp system can serve as the sole source only of phosphate but not of carbon, while GlpT-transported G3P can serve as the sole source for both (Schweizer et al., *J. Bacteriol.*, 150: 1154-1163 (1982)). The two ugp genes coding for the pho-regulon-dependent G3P transport system have been mapped (Schweizer et al., *J. Bacteriol.*, 150: 1164-1171 (1982)), the ugp region containing these genes has been characterized (Schweizer et al., *Mol. and Gen. Genetics*, 197: 161-168 (1984)), and the regulation of ugp operon studied (Schweizer et al., *J. Bacteriol.*, 163: 392-394 (1985); Kasahara et al., *J. Bacteriol.*, 173: 549-558 (1991); Su et al., *Molecular & General Genetics*, 230: 28-32 (1991); Brzoska et al., "ugp-dependent transport system for sn-glycerol 3-phosphate of *Escherichia coli*," p. 170-177 in A. Torriani-Gorini, F. G. Rothman, S. Silver, A. Wright, and E. Yagil (ed.), *Phosphate Metabolism and Cellular Regulation in Microorganisms* (American Society for Microbiology, Washington, D.C., 1987); Brzoska et al., *J. Bacteriol.*, 176: 15-20 (1994); and Xavier et al., *J. Bacteriol.*, 177: 699-704 (1995)).

In wild-type strains, there exists a stable intracellular pool of G3P and it is maintained at approximately 200 μM. Internally, G3P can be synthesized by the enzymatic conversion of glycerol by glycerol kinase (encoded by glpK) to G3P when grown on glycerol as the sole carbon source, or from the reduction of the glycolytic intermediate, dihydroxyactone phosphate, by G3P synthase, the gene product of the gpsA gene, during growth on carbon sources other than glycerol. Since G3P is an important intermediate that forms the scaffold of all phospholipid molecules, internal glycerol phosphates may also be generated from the breakdown of phospholipids and triacylglycerol. As a metabolite, internal G3P may be channeled into the phospholipid biosynthetic pathway or be oxidized by G3P dehydrogenase to form dihydroxyacetone phosphate and fed into the glycolytic pathway.

In situations where the AP promoter is employed for regulating heterologous protein expression in *E. coli*, since induction occurs only after the medium is depleted of Pi, cells induced for AP promoter activity are typically starved for phosphate and in a declining state of health. They may have to scavenge for phosphate needed for cellular functions. Possible consequences of such phosphate scavenging may include turnover of ribosomes, lower cell energetics, and increased protease expression and proteolysis (St. John and Goldberg, *J. Bacteriol.*, 143: 1223-1233 (1980)), potentially leading to less healthy cells with reduced capacity for protein accumulation.

Improving the metabolic state of *E. coli* may conceivably increase the capacity of the cell to synthesize proteins. If phosphate is fed slowly, the cells may only sense low Pi concentration in the periplasm, thereby inducing the pho regulon without being starved intracellularly for the P atom (see U.S. Pat. No. 5,304,472). There is a need for providing further methods of producing heterologous polypeptides in *E. coli*.

SUMMARY OF THE INVENTION

In the invention herein, a process is provided for improving the expression of heterologous polypeptides in *E. coli*. The feeding of transportable organophosphate such as an alpha-glycerophosphate to various *E. coli* hosts, including those with and without the wild-type glpT gene and those with and without the wild-type phoA gene, such as, for example, (ugp+ ΔglpT phoA−) *E. coli*, is shown to improve the expression of heterologous protein at both shake-flask and 10-L-fermentor scale, and is expected to perform similarly at larger scale such as 10,000 L. Product yield benefit was observed across multiple model systems that employed a variety of promoters, including inducible promoters such as the tac, T7 or AP promoter, for the expression of the heterologous proteins. A further advantage is that the product can be obtained earlier in the active growth phase, i.e., in a shorter time than otherwise. In certain embodiments, more product can be obtained earlier in the active growth phase to improve productivity significantly.

Accordingly, the present invention is as claimed. In one aspect the present invention provides a process for producing a polypeptide heterologous to *E. coli* comprising (a) culturing *E. coli* cells comprising nucleic acid encoding the polypeptide in a culture medium while feeding to the culture medium a transportable organophosphate, such that the nucleic acid is expressed, and (b) recovering the polypeptide from the cells. In a preferred embodiment, the organophosphate is a glycerophosphate, more preferably, an alpha-glycerophosphate and/or a beta-glycerophosphate, and still more preferably, a mixture of glycerol-2-phosphate and glycerol-3-phosphate or glycerol-3-phosphate alone. In another preferred aspect, the culturing takes place in a shake flask or fermentor, preferably a fermentor. In yet another preferred embodiment, the polypeptide is recovered from the cytoplasm, periplasm, or culture medium of the cells. Also preferred is that expression of the nucleic acid is regulated by an inducible promoter, such as alkaline phosphatase promoter, tac promoter, or Ti promoter, and preferably wherein expression of the nucleic acid begins while in the active growth phase of the culturing step. In one embodiment, the *E. coli* is wild type. In another embodiment, the *E. coli* is deficient in chromosomal glpT and in chromosomal phoA, but preferably not deficient in chromosomal ugp. Preferably an inorganic phosphate is also present during the culturing step.

Without being limited to any one theory, it is believed that in this process the transportable organophosphate compounds are fed to the cells such that the phosphate supply will not be sensed by the pstS of the Pho system but will still provide phosphate upon breakdown in the cytoplasm, and further that feeding transportable organophosphate such as G3P potentially enriches the cells with a utilizable metabolic intermediate that can be readily fed into important metabolic pathways.

BRIEF DESCRIPTION OF THE DRAWINGS

FIG. 1 shows expression of a secreted llama antibody fragment in a BL21 *E. coli* host using the tac promoter in a shake-flask culture, utilizing either water or 200 mM G3P as a supplement in low-phosphate (CRAP) or high-phosphate (THCD) medium.

FIG. 2 shows expression of a cytoplasmic Apo2L in a HMS174 *E. coli* host using the T7 promoter in a shake-flask culture, utilizing either water or 200 mM G3P as a supplement in CRAP medium.

FIG. 3 shows the effect of feeding of G3P during fermentation on secreted IGF-1 accumulation over time. This uses a wild-type *E. coli* host, the AP promoter, and continuously fed glucose.

FIG. 4 shows the effect of a glpT mutation and G3P feeding during fermentation on secreted IGF-1 accumulation over time. This uses a ΔglpT *E. coli* host, the AP promoter, and varying G3P feed rate.

FIG. 5 shows the plasmid diagram for pAPApo2-P2RU.

FIG. 6 shows the nucleotide sequence of human Apo-2 ligand cDNA (SEQ ID NO:1) and its derived amino acid sequence (SEQ ID NO:2). The "N" at nucleotide position 447 (in SEQ ID NO:1) is used to indicate the nucleotide base may be a "T" or "G".

FIG. 7 shows the effect of G3P feeding on specific accumulation of Apo2L in the ΔglpT *E. coli* (43F6) host, with three different feed rates and a control with no G3P feed.

FIG. 8 shows the benefit on the specific total accumulation of Apo2L of feeding glycerophosphate over inorganic phosphate to the wild-type glpT host (43E7), wherein the cell density increases to over 200 OD550.

FIG. 9 shows the effect on specific total accumulation of Apo2L of replacement of inorganic phosphate with glycerophosphate in the wild-type glpT *E. coli* host (43E7) and ΔglpT *E. coli* (43F6) host.

FIG. 10 shows the effect on total Apo2L accumulation of replacement of alpha-glycerophosphate with a 50:50 mixture of alpha- and beta-glycerophosphate as a feed, versus a no-feed control, in a ΔglpT *E. coli* (61G1) host.

DETAILED DESCRIPTION OF THE PREFERRED EMBODIMENTS

Definitions

As used herein, "polypeptide" refers generally to peptides and proteins having more than about ten amino acids. "Heterologous" polypeptides are those polypeptides foreign to the host cell being utilized, such as a human protein produced by *E. coli*. While the polypeptide may be prokaryotic or eukaryotic, preferably it is eukaryotic, more preferably mammalian, and most preferably human.

Examples of mammalian polypeptides include molecules such as, e.g., rennin; a growth hormone, including human growth hormone or bovine growth hormone; growth-hormone releasing factor; parathyroid hormone; thyroid-stimulating hormone; lipoproteins; 1-antitrypsin; insulin A-chain; insulin B-chain; proinsulin; thrombopoietin; follicle-stimulating hormone; calcitonin; luteinizing hormone; glucagon; clotting factors such as factor VIIIC, factor IX, tissue factor, and von Willebrands factor; anti-clotting factors such as Protein C; atrial naturietic factor; lung surfactant; a plasminogen activator, such as urokinase or human urine or tissue-type plasminogen activator (t-PA); bombesin; thrombin; hemopoietic growth factor; tumor necrosis factor-alpha and -beta; antibodies to ErbB2 domain(s) such as 2C4 (WO 01/00245; hybridoma ATCC HB-12697), which binds to a region in the extracellular domain of ErbB2 (e.g., any one or more residues in the region from about residue 22 to about residue 584 of ErbB2, inclusive); enkephalinase; mullerian-inhibiting substance; relaxin A-chain; relaxin B-chain; prorelaxin; mouse gonadotropin-associated peptide; a microbial protein, such as beta-lactamase; DNase; inhibin; activin; vascular endothelial growth factor (VEGF); receptors for hormones or growth factors; integrin; protein A or D; rheumatoid factors; a neurotrophic factor such as brain-derived neurotrophic factor (BDNF), neurotrophin-3, -4, -5, or -6 (NT-3, NT-4, NT-5, or NT-6), or a nerve growth factor such as NGF; cardiotrophins (cardiac hypertrophy factor) such as cardiotrophin-1 (CT-1); platelet-derived growth factor (PDGF); fibroblast growth factor such as aFGF and bFGF; epidermal growth factor (EGF); transforming growth factor (TGF) such as TGF-alpha and TGF-beta, including TGF-1, TGF-2, TGF-3, TGF-4, or TGF-5; insulin-like growth factor-I and -II (IGF-I and IGF-II); des(1-3)-IGF-I (brain IGF-I); insulin-like growth factor binding proteins; CD proteins such as CD-3, CD-4, CD-8, and CD-19; erythropoietin; osteoinductive factors; immunotoxins; a bone morphogenetic protein (BMP); an interferon such as interferon-alpha, -beta, and -gamma; a serum albumin, such as human serum albumin (HSA) or bovine serum albumin (BSA); colony stimulating factors (CSFs), e.g., M-CSF, GM-CSF, and G-CSF; interleukins (ILs), e.g., IL-1 to IL-10; anti-HER-2 antibody; Apo2 ligand (Apo2L); superoxide dismutase; T-cell receptors; surface-membrane proteins; decay-accelerating factor; viral antigens such as, for example, a portion of the AIDS envelope; transport proteins; homing receptors; addressins; regulatory proteins; antibodies; and fragments of any of the above-listed polypeptides.

The preferred polypeptides of interest include polypeptides such as HSA, BSA, anti-IgE, anti-CD20, anti-IgG, t-PA, gp120, anti-CD11a, anti-CD18, 2C4, anti-VEGF, VEGF, TGF-beta, activin, inhibin, anti-HER-2, DNase, IGF-I, IGF-II, brain IGF-I, growth hormone, relaxin chains, growth-hormone releasing factor, insulin chains or pro-insulin, antibodies and antibody fragments, NGF, NT-3, BDNF; Apo2L, and urokinase. The polypeptide is most preferably IGF-I or Apo2L.

The terms "Apo2 ligand," "Apo2L," and "TRAIL" are used herein interchangeably to refer to a polypeptide sequence that includes amino acid residues 114-281, inclusive, residues 95-281, inclusive, residues 92-281, inclusive, residues 91-281, inclusive, residues 41-281, inclusive, residues 15-281, inclusive, or residues 1-281, inclusive, of the amino acid sequence shown in FIG. 6 (SEQ ID NO:2), as well as biologically active fragments, and deletional, insertional, or substitutional variants of the above sequences. In one embodiment, the polypeptide sequence comprises residues 114-281 of FIG. 6 (SEQ ID NO:2). Optionally, the polypeptide sequence comprises residues 92-281 or residues 91-281 of FIG. 6 (SEQ ID NO:2). The Apo2L polypeptides may be encoded by the native nucleotide sequence shown in FIG. 6 (SEQ ID NO:1). Optionally, the codon that encodes residue Pro119 (FIG. 6; SEQ ID NO:1) may be "CCT" or "CCG." In another preferred embodiment, the fragments or variants are biologically active and have at least about 80% amino acid sequence identity, more preferably at least about 90% sequence identity, and even more preferably, at least 95%, 96%, 97%, 98%, or 99% sequence identity, with any one of the above sequences. The definition encompasses substitutional variants of Apo2 ligand in which at least one of its native amino acids is substituted by an alanine residue. The definition also encompasses a native-sequence Apo2 ligand isolated from an Apo2 ligand source or prepared by recombinant or synthetic methods. The Apo2 ligand of the invention includes the polypeptides referred to as Apo2 ligand or TRAIL disclosed in WO 97/01633, WO 97/25428, and WO 01/00832. The terms "Apo2 ligand" and "Apo2L" are used to refer generally to forms of the Apo2 ligand that include monomer, dimer, or trimer forms of the polypeptide. All numbering of amino acid residues referred to in the Apo2L sequence uses the numbering according to FIG. 6 (SEQ ID NO:2) unless specifically stated otherwise. For instance, "D203" or "Asp203" refers to the aspartic acid residue at position 203 in the sequence provided in FIG. 6 (SEQ ID NO:2).

The term "Apo-2 ligand extracellular domain" or "Apo2 ligand ECD" refers to a form of Apo2 ligand that is essentially free of transmembrane and cytoplasmic domains. Ordinarily, the ECD will have less than 1% of such transmembrane and cytoplasmic domains, and preferably will have less than 0.5% of such domains. "Biologically active" or "biological activity," as it relates to Apo2L, refers to (a) having the ability to induce or stimulate apoptosis in at least one type of mammalian cancer cell or virally infected cell in vivo or ex vivo; (b) capable of raising an antibody (i.e., immunogenic), (c) capable of binding and/or stimulating a receptor for Apo2L; or (d) retaining the activity of a native or naturally occurring Apo2L polypeptide.

The expression "control sequences" refers to DNA sequences necessary for the expression of an operably linked coding sequence in a particular host organism. The control sequences that are suitable for prokaryotes include a promoter, optionally an operator sequence, and a ribosome-binding site.

Nucleic acid is "operably linked" when it is placed into a functional relationship with another nucleic acid sequence.

For example, DNA for a presequence or secretory leader is operably linked to DNA for a polypeptide if it is expressed as a pre-protein that participates in the secretion of the polypeptide; a promoter is operably linked to a coding sequence if it affects the transcription of the sequence; or a ribosome-binding site is operably linked to a coding sequence if it is positioned so as to facilitate translation. Generally, "operably linked" means that the DNA sequences being linked are contiguous, and, in the case of a secretory leader, contiguous and in reading phase. Linking is accomplished by ligation at convenient restriction sites. If such sites do not exist, the synthetic oligonucleotide adaptors or linkers may be used in accordance with conventional practice.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

The term "organophosphate" as used herein refers to a phosphate compound containing one or more carbon atoms, which can also contain halide atoms. Such phosphate compound must be such that it can be fed to and utilized by a cell culture. These compounds are often used as pesticides. "Transportable" organophosphates can be transported from the external environment of the cell into the cell without having to be pre-hydrolyzed in any way. If an *E. coli* strain does not grow well with an organophosphate, the utilization of such organophosphate can be enhanced by overexpressing in *E. coli* the phnE gene product. Such gene confers the spontaneous organophosphate utilization phenotype to the *E. coli* strain upon transformation. See Elashvili et al., supra. Examples of suitable organophosphates include alkyl halophosphates such as diisopropyl fluorophosphate, alkyl phosphates such as diisopropyl phosphate and 3,4-dihydroxybutyl-1-phosphate, as well as sugar- or alkanol-containing phosphates such as hexose-6-phosphate and glycerol-3-phosphate. Glucose-1-phosphate, hexose-6-phosphate and glycerophosphates such as glucose-1-glycerophosphate, fructose-6-glycerophosphate, alpha-glycerophosphates such as glycerol-1-phosphate and glycerol-3-phosphate, and beta-glycerophosphate (glycerol-2-phosphate) are preferred, with glycerophosphates more preferred, alpha- and/or beta-glycerophosphates still more preferred, and glycerol-2-phosphate and/or glycerol-3-phosphate still more preferred, and a mixture of glycerol-2- and glycerol-3-phosphate or glycerol-3-phosphate most particularly preferred herein for use. As used herein, the term "G3P" without being in a mixture or "G3P alone" refers to a composition containing at least about 80% glycerol-3-phosphate; it may contain up to about 20% impurities such as G2P. A mixture of G3P and G2P would contain less than about 80% G3P.

An inorganic phosphate is a phosphate compound that does not contain any carbon atoms, with the phosphate typically being associated with an alkali or alkali earth metal such as potassium, calcium, magnesium, or sodium phosphate.

"Active growth phase" refers to the phase of the culturing step wherein the cells are actively growing and not severely nutrient-limited cells such as those that are in stationary phase.

Modes for Carrying Out the Invention

The present invention provides a method for producing polypeptides heterologous to *E. coli*. In this method *E. coli* cells comprising nucleic acid encoding the polypeptide are cultured in a culture medium while feeding to the culture medium a transportable organophosphate, such that the nucleic acid is expressed. The polypeptide is then recovered from the cells. The recovery may be from the cytoplasm, periplasm, or culture medium of the cells. The culturing may take place in any suitable vessel, preferably a shake flask or fermentor, more preferably, in a fermentor.

Culturing parameters are used and polypeptide production may be conducted in a conventional manner, such as those procedures described below.

A. Selection of Nucleic Acid and Modifications Thereof

The nucleic acid encoding the polypeptide of interest is suitably RNA, cDNA, or genomic DNA from any source, provided it encodes the polypeptide(s) of interest. Methods are well known for selecting the appropriate nucleic acid for expression of heterologous polypeptides (including variants thereof) in *E. coli*.

If monoclonal antibodies are being produced, DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transformed into the bacterial host cells herein to obtain the synthesis of monoclonal antibodies in the recombinant host cells. Review articles on recombinant expression in bacteria of DNA encoding the antibody include Skerra et al., *Curr. Opinion in Immunol.*, 5: 256-262 (1993) and Plückthun, *Immunol. Revs.*, 130: 151-188 (1992).

Methods for humanizing non-human antibodies have been described in the art. Preferably, a humanized antibody has one or more amino acid residues introduced into it from a source that is non-human. These non-human amino acid residues are often referred to as "import" residues, which are typically taken from an "import" variable domain. Humanization can be essentially performed following the method of Winter and co-workers (Jones et al., *Nature*, 321: 522-525 (1986); Riechmann et al., *Nature*, 332: 323-327 (1988); Verhoeyen et al., *Science*, 239: 1534-1536 (1988)), by substituting hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some hypervariable region residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence that is closest to that of the rodent is then accepted as the human framework region (FR) for the humanized antibody (Sims et al., *J. Immunol.*, 151: 2296 (1993); Chothia et al., *J. Mol. Biol.*, 196: 901 (1987)). Another method uses a particular framework region derived from the consensus sequence of all human antibodies of a particular subgroup of light or heavy chains. The same framework may be used for several different humanized antibodies (Carter et al., *Proc. Natl. Acad. Sci. USA*, 89: 4285 (1992); Presta et al., *J. Immunol.*, 151: 2623 (1993)).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available that illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

Various forms of the humanized antibody or affinity-matured antibody are contemplated. For example, the humanized antibody or affinity-matured antibody may be an antibody fragment, such as a Fab, that is optionally conjugated with one or more targeting agent(s) in order to generate an immunoconjugate. Alternatively, the humanized antibody or affinity-matured antibody may be an intact antibody, such as an intact IgG1 antibody.

Fab'-SH fragments can be directly recovered from *E. coli* and chemically coupled to form F(ab')$_2$ fragments (Carter et al., *Bio/Technology*, 10: 163-167 (1992)). According to another approach, F(ab')$_2$ fragments can be isolated directly from recombinant host cell culture. Other techniques for the production of antibody fragments will be apparent to the skilled practitioner. In other embodiments, the antibody of choice is a single-chain Fv fragment (scFv) (WO 93/16185; U.S. Pat. Nos. 5,571,894 and 5,587,458). The antibody fragment may also be a "linear antibody", e.g., as described in U.S. Pat. No. 5,641,870. Such linear antibody fragments may be monospecific or bispecific.

Bispecific antibodies are antibodies that have binding specificities for at least two different epitopes. Exemplary bispecific antibodies may bind to two different epitopes of the same protein. Bispecific antibodies can be prepared as full-length antibodies or antibody fragments (e.g., F(ab')$_2$ bispecific antibodies). These may be as fusions of various antibody chains or can be one chain. One heavy chain can be competent by itself.

In one approach to producing bispecific antibodies, a bispecific immunoadhesin is prepared by introducing into a host cell DNA sequences encoding a first fusion comprising a first binding domain fused to an immunoglobulin heavy-chain constant domain sequence lacking a light-chain binding site; a second fusion comprising a second binding domain fused to an immunoglobulin heavy-chain constant domain sequence retaining a light-chain binding site; and an immunoglobulin light-chain, respectively. The host cells are then cultured so as to express the DNA sequences to produce a mixture of (i) a heterotrimer comprising the first fusion covalently linked with a second fusion-immunoglobulin light-chain pair; (ii) a heterotetramer comprising two covalently linked second fusion-immunoglobulin light-chain pairs; and (iii) a homodimer comprising two covalently linked molecules of the first fusion. The mixture of products is removed from the cell culture and the heterotrimer is isolated from the other products. This approach is disclosed in WO 94/04690. For further details of generating bispecific antibodies see, for example, Suresh et al., *Methods in Enzymology*, 121: 210 (1986).

According to another approach described in U.S. Pat. No. 5,731,168, the interface between a pair of antibody molecules can be engineered to maximize the percentage of heterodimers that are recovered from recombinant cell culture. The preferred interface comprises at least a part of the $C_H3$ domain of an antibody constant domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed, for example, in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., *Science*, 229: 81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Additionally, Fab'-SH fragments can be directly recovered from *E. coli* and chemically coupled to form bispecific antibodies (Shalaby et al., *J. Exp. Med.*, 175: 217-225 (1992)).

Various techniques for making and isolating bispecific antibody fragments directly from recombinant cell culture have also been described. For example, bispecific antibodies have been produced using leucine zippers (Kostelny et al., *J. Immunol.*, 148: 1547-1553 (1992)). The leucine zipper peptides from the Fos and Jun proteins are linked to the Fab' portions of two different antibodies by gene fusion. The antibody homodimers are reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA*, 90: 6444-6448 (1993) has provided an alternative mechanism for making bispecific antibody fragments. The fragments comprise a heavy-chain variable domain ($V_H$) connected to a light-chain variable domain ($V_L$) by a linker that is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported (Gruber et al., *J. Immunol.*, 152: 5368 (1994)).

Antibodies with more than two valencies are contemplated. For example, trispecific antibodies can be prepared (Tutt et al., *J. Immunol.*, 147: 60 (1991)).

Nucleic acid molecules encoding polypeptide variants are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, or cassette mutagenesis of an earlier prepared variant or a non-variant version of the polypeptide.

It may be desirable to modify the antibody of the invention with respect to effector function, e.g., so as to enhance Fc receptor binding. This may be achieved by introducing one or more amino acid substitutions into an Fc region of the antibody. Alternatively or additionally, cysteine residue(s) may be introduced in the Fc region, thereby allowing interchain disulfide bond formation in this region.

To increase the serum half-life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., $IgG_1$, $IgG_2$, $IgG_3$, or $IgG_4$) that is responsible for increasing the in vivo serum half-life of the IgG molecule.

Other modifications of the antibody are contemplated herein. For example, the antibody may be linked to one of a variety of non-proteinaceous polymers, e.g., polyethylene glycol, polypropylene glycol, polyoxyalkylenes, or copolymers of polyethylene glycol and polypropylene glycol.

B. Insertion of Nucleic Acid into a Replicable Vector

The heterologous nucleic acid (e.g., cDNA or genomic DNA) is suitably inserted into a replicable vector for expression in the *E. coli* under the control of a suitable promoter. Many vectors are available for this purpose, and selection of the appropriate vector will depend mainly on the size of the nucleic acid to be inserted into the vector and the particular host cell to be transformed with the vector. Each vector contains various components depending on the particular host cell with which it is compatible. Depending on the particular type of host, the vector components generally include, but are not limited to, one or more of the following: a signal sequence, an origin of replication, one or more marker genes, a promoter, and a transcription termination sequence.

In general, plasmid vectors containing replicon and control sequences that are derived from species compatible with the host cell are used in connection with *E. coli* hosts. The vector ordinarily carries a replication site, as well as marking sequences that are capable of providing phenotypic selection in transformed cells. For example, *E. coli* is typically transformed using pBR322, a plasmid derived from an *E. coli* species (see, e.g., Bolivar et al., *Gene*, 2: 95 (1977)). pBR322 contains genes for ampicillin and tetracycline resistance and thus provides easy means for identifying transformed cells. The pBR322 plasmid, or other bacterial plasmid or phage, also generally contains, or is modified to contain, promoters that can be used by the *E. coli* host for expression of the selectable marker genes.

(i) Signal Sequence Component

The DNA encoding the polypeptide of interest herein may be expressed not only directly, but also as a fusion with another polypeptide, preferably a signal sequence or other polypeptide having a specific cleavage site at the N-terminus of the mature polypeptide. In general, the signal sequence may be a component of the vector, or it may be a part of the polypeptide-encoding DNA that is inserted into the vector. The heterologous signal sequence selected should be one that is recognized and processed (i.e., cleaved by a signal peptidase) by the host cell.

For prokaryotic host cells that do not recognize and process the native or a eukaryotic polypeptide signal sequence, the signal sequence is substituted by a prokaryotic signal sequence, selected, for example, from the group consisting of the alkaline phosphatase, penicillinase, lpp, or heat-stable enterotoxin II leaders.

(ii) Origin of Replication Component

Expression vectors contain a nucleic acid sequence that enables the vector to replicate in one or more selected host cells. Such sequences are well known for a variety of bacteria. The origin of replication from the plasmid pBR322 is suitable for most Gram-negative bacteria such as *E. coli*.

(iii) Selection Gene Component

Expression vectors generally contain a selection gene, also termed a selectable marker. This gene encodes a protein necessary for the survival or growth of transformed host cells grown in a selective culture medium. Host cells not transformed with the vector containing the selection gene will not survive in the culture medium. This selectable marker is separate from the genetic markers as utilized and defined by this invention. Typical selection genes encode proteins that (a) confer resistance to antibiotics or other toxins, e.g., ampicillin, neomycin, methotrexate, or tetracycline, (b) complement auxotrophic deficiencies other than those caused by the presence of the genetic marker(s), or (c) supply critical nutrients not available from complex media, e.g., the gene encoding D-alanine racemase for Bacilli.

One example of a selection scheme utilizes a drug to arrest growth of a host cell. In this case, those cells that are successfully transformed with the nucleic acid of interest produce a polypeptide conferring drug resistance and thus survive the selection regimen. Examples of such dominant selection use the drugs neomycin (Southern et al., *J. Molec. Appl. Genet.*, 1: 327 (1982)), mycophenolic acid (Mulligan et al., *Science*, 209: 1422 (1980)), or hygromycin (Sugden et al., *Mol. Cell. Biol.*, 5: 410-413 (1985)). The three examples given above employ bacterial genes under eukaryotic control to convey resistance to the appropriate drug G418 or neomycin (geneticin), xgpt (mycophenolic acid), or hygromycin, respectively.

(iv) Promoter Component

The expression vector for producing the polypeptide of interest contains a suitable promoter that is recognized by *E. coli* and is operably linked to the nucleic acid encoding the polypeptide of interest. Promoters suitable for use with *E. coli* hosts include the beta-lactamase and lactose promoter systems (Chang et al., *Nature*, 275: 615 (1978); Goeddel et al., *Nature*, 281: 544 (1979)), the arabinose promoter system (Guzman et al., *J. Bacteriol.*, 174: 7716-7728 (1992)), alkaline phosphatase, the T7 promoter, a tryptophan (trp) promoter system (Goeddel, *Nucleic Acids Res.*, 8: 4057 (1980) and EP 36,776) and hybrid promoters such as the tac promoter (deBoer et al., *Proc. Natl. Acad. Sci. USA*, 80: 21-25 (1983)). However, other known bacterial promoters are suitable. Their nucleotide sequences have been published, thereby enabling a skilled worker operably to ligate them to DNA encoding the polypeptide of interest (Siebenlist et al., *Cell*, 20: 269 (1980)) using linkers or adaptors to supply any required restriction sites.

Preferably, the promoter employed herein is an inducible promoter, i.e., one that is activated by an inducing agent or condition (such as periplasmic phosphate depletion). Preferred such inducible promoters herein are the alkaline phosphatase promoter, the tac promoter, or the T7 promoter.

Promoters for use in bacterial systems also generally contain a Shine-Dalgarno (S.D.) sequence operably linked to the DNA encoding the polypeptide of interest. The promoter can be removed from the bacterial source DNA by restriction enzyme digestion and inserted into the vector containing the desired DNA.

(v) Construction and Analysis of Vectors

Construction of suitable vectors containing one or more of the above-listed components employs standard ligation techniques. Isolated plasmids or DNA fragments are cleaved, tailored, and re-ligated in the form desired to generate the plasmids required.

For analysis to confirm correct sequences in plasmids constructed, the ligation mixtures are used to transform *E. coli* K12 strain 294 (ATCC 31,446) or other strains, and successful transformants are selected by ampicillin or tetracycline resistance where appropriate. Plasmids from the transformants are prepared, analyzed by restriction endonuclease digestion, and/or sequenced by the method of Sanger et al., *Proc. Natl. Acad. Sci. USA,* 74: 5463-5467 (1977) or Messing et al., *Nucleic Acids Res.,* 9: 309 (1981), or by the method of Maxam et al., *Methods in Enzymology,* 65: 499 (1980).

C. Selection and Transformation of Host Cells

*E. coli* hosts suitable as parental hosts for expression plasmids herein include *E. coli* W3110 (ATCC 27,325), *E. coli* 294 (ATCC 31,446), *E. coli* B, and *E. coli* X1776 (ATCC 31,537). These examples are illustrative rather than limiting. Mutant cells of any of the above-mentioned strains may also be employed as the starting hosts that are then further mutated to contain at least the minimum genotype required herein. *E. coli* strain W3110 is a preferred parental host because it is a common host strain for recombinant DNA product fermentations. Examples of starting *E. coli* hosts to be used as parent hosts, along with their genotypes, are included in the table below:

In another embodiment, the *E. coli* host cell employed is wild type with respect to or in reference to the phoA gene. In a preferred embodiment, the *E. coli* is deficient in chromosomal phoA. In another preferred embodiment, the *E. coli* is deficient in chromosomal glpT and in chromosomal phoA. In a more preferred embodiment, the *E. coli* is deficient in chromosomal glpT and in chromosomal phoA, but not in chromosomal ugp. The most preferred such mutant *E. coli* host is 43F6 or 61G1, the genotypes of which are given in the above table. As used herein, "wild type with respect to glpT" refers to *E. coli* hosts that are glpT+ or glpT competent cells, i.e., those that are not deficient in chromosomal glpT. Similarly, as used herein, "wild type with respect to phoA" refers to *E. coli* hosts that are phoA+ or phoA competent cells, i.e., those that are not deficient in chromosomal phoA.

The strains of this invention may be produced by chromosomal integration of the parental strain or other techniques, including those set forth in the Examples below.

The nucleic acid encoding the polypeptide is inserted into the host cells. Preferably, this is accomplished by transforming the host cells with the above-described expression vectors and culturing in conventional nutrient media modified as appropriate for inducing the various promoters.

Transformation means introducing DNA into an organism so that the DNA is replicable, either as an extrachromosomal element or by chromosomal integrant. Depending on the host cell used, transformation is done using standard techniques appropriate to such cells. The calcium treatment employing calcium chloride, as described in section 1.82 of Sambrook et al., *Molecular Cloning: A Laboratory Manual* (New York: Cold Spring Harbor Laboratory Press, 1989), is generally used for prokaryotic cells or other cells that contain substantial cell-wall barriers. Another method for transformation employs polyethylene glycol/DMSO, as described in Chung and Miller, *Nucleic Acids Res.,* 16: 3580 (1988). Yet another method is the use of the technique termed electroporation.

D. Culturing the Host Cells

*E. coli* cells used to produce the polypeptide of interest are cultured in suitable media as described generally in Sam-

| Strain | Genotype |
|---|---|
| W3110 | K-12 F⁻ lambda⁻ IN(rrnD-rrnE)1 |
| 1A2 | ΔfhuA (ΔtonA) |
| 9E4 | ΔfhuA (ΔtonA) ptr3 |
| 27A7 | ΔfhuA (ΔtonA) ptr3 phoAΔE15 (argF-lac)169 |
| 27C6 | ΔfhuA (ΔtonA) phoAΔE15 (argF-lac)169 ptr3 ompT Δ (nmpc-fepE) |
| 27C7 | ΔfhuA (ΔtonA) phoAΔE15 (argF-lac)169 ptr3 degP41::kanR ompT Δ(nmpc-fepE) |
| 33D3 | ΔfhuA (ΔtonA) ptr3 lacIq lacL8 ompT Δ(nmpc-fepE) degP::kanR |
| 36F8 | ΔfhuA (ΔtonA) phoAΔE15 (argF-lac)169 ptr3 degP41::kanR ilvG+ |
| 43D3 | ΔfhuA (ΔtonA) phoAΔE15 (argF-lac)169 ptr3 degP41::kanR ompT Δ(nmpc-fepE) ilvG+ |
| 43E7 | ΔfhuA (ΔtonA) phoAΔE15 (argF-lac)169 ptr3 degP41 ompT Δ(nmpc-fepE) ilvG+ |
| 43F6 | ΔfhuA (ΔtonA) phoAΔE15 (argF-lac)169 ptr3 degP41::kanR ompT Δ(nmpc-fepE) Δ(rbs7) ilvG+ ΔglpT596 |
| 44D6 | ΔfhuA (ΔtonA) (argF-lac)169 ptr3 degP41::kanR ompT Δ(nmpc-fepE) ilvG+ |
| 45F8 | ΔfhuA (ΔtonA) (argF-lac)169 ptr3 degP41 ompT Δ(nmpc-fepE) ilvG+ phoS(T10Y) |
| 45F9 | ΔfhuA (ΔtonA) (argF-lac)169 ptr3 degP41 ompT Δ(nmpc-fepE) ilvG+ phoS(T10Y) cyo::kanR |
| 61G1 | ΔfhuA Δptr ΔompT ΔdegP ΔphoA ilvG+ ΔglpTQ |

Also suitable are the intermediates in making strain 36F8, i.e., 27B4 (U.S. Pat. No. 5,304,472) and 35E7 (a spontaneous temperature-resistant colony isolate growing better than 27B4). An additional suitable strain is the *E. coli* strain having the mutant periplasmic protease(s) disclosed in U.S. Pat. No. 4,946,783 issued Aug. 7, 1990.

In one embodiment, the *E. coli* host cell employed is wild type with respect to or in reference to the glpT gene, such as 43E7, or is deficient in the glpT gene, such as 43F6 or 61G1.

brook et al., supra. The culture conditions, such as temperature, pH, and the like, are those previously used with the host cell selected for expression, and will be apparent to the ordinarily skilled artisan.

The cells are cultured while the culture medium is fed with a transportable organophosphate such as a glycerophosphate, e.g., alpha-glycerophosphate and/or beta-glycerophosphate, and especially glycerol-2-phosphate and/or glycerol-3-phosphate. The culturing may take place in a shake flask or a fermentor, preferably a fermentor. The polypeptide is preferably recovered from the cytoplasm, periplasm, or culture medium of the cells.

In the process of this invention, expression of the nucleic acid can begin at any phase of the culturing step. However, preferably expression of the nucleic acid begins while cell density is still increasing. This can be accomplished by the inducement of the promoter with the appropriate inducer or inducing condition before cell growth ceases.

The feed rate of the organophosphate into the culture medium to be employed for maximum production of the polypeptide depends on many factors, including the type of organophosphate, the concentration of organophosphate, the type of polypeptide being produced, the type of promoter, the host cell strain employed, and the cell density in the broth. If the polypeptide is IGF-I and the organophosphate is glycerol-3-phosphate intended to extend the production duration, under the culture conditions described and using a 10-L process, the feed rate of the organophosphate is preferably from about 1 to 7 mmoles/hour per about 8-10 liters (see FIG. 4), more preferably from about 1 to 6 mmoles/hour, and still more preferably from about 2 to 6 mmoles/hour, yet still more preferably from about 2 to 5 mmoles/hour, and most preferably from about 3 to 4 mmoles/hour. The optimal feed rate is dependent on the process, the cell density, the respiration rate, etc.

Also, in a preferred embodiment, where the polypeptide is Apo2L and the organophosphate is glycerol-3-phosphate intending to shift product expression to concur with the active growth phase and using a 10-L process, the feed rate of the organophosphate is from about 4 to 17 mmoles/hour per about 8-10 liters (see FIG. 7), more preferably from about 6 to 16 mmoles/hour, still more preferably from about 8 to 15 mmoles/hour, and most preferably from about 10 to 14 mmoles/hour. The optimal feed rate of the organophosphate needs to be determined for the individual process employed for the expression of the specific heterologous protein.

Any other necessary media ingredients besides carbon, nitrogen, and inorganic phosphate sources may also be included at appropriate concentrations introduced alone or as a mixture with another ingredient or medium such as a complex nitrogen source. Preferably, an inorganic phosphate is also present in the culture medium at the start of the culturing step. If such inorganic phosphate, preferably sodium and/or potassium phosphate, is present, the ratio of inorganic phosphate to organophosphate depends on such factors as the type of polypeptide expressed and organophosphate employed. This ratio can be any proportion, as determined readily by those skilled in the art, ranging typically from about 1:10 (one part of Pi to 10 parts of organophosphate) to 1:0.25. For Apo2 ligand, preferably it ranges from about 1:4 to 1:0.25, and more preferably about 1:3 to 1:0.5, and yet more preferably about 1:3 to 1:1, and still mere preferably about 1:2 to 1:1, and most preferably about 1:1. Such ratios allow earlier induction of protein expression, and in some cases allow more product to be produced earlier. The pH of the medium may be any pH from about 5-9, depending mainly on the host organism.

If the promoter is an inducible promoter, for induction to occur, typically the cells are cultured until a certain optical density is achieved, e.g., a $A_{550}$ of about 200 for a high-cell-density process, at which point induction is initiated (e.g., by addition of an inducer, by depletion of a medium component, etc.), to induce expression of the gene encoding the polypeptide of interest.

Where the alkaline phosphatase promoter is employed, *E. coli* cells used to produce the polypeptide of interest of this invention are cultured in suitable media in which the alkaline phosphatase promoter can be induced as described generally, e.g., in Sambrook et al., supra. At first, the medium may contain inorganic phosphate for the growth of the bacterium in an amount sufficiently large to support significant cell growth and avoid induction of synthesis of target heterologous polypeptide under the promoter control. As the cells grow and utilize phosphate, they decrease the level of inorganic phosphate in the medium, thereby causing induction of synthesis of the polypeptide when the inorganic phosphate is exhausted. By adding, for example, a feed constituting a mixture of G2P and G3P or a G3P feed, further growth to a higher cell density, such as up to 200 OD550 or higher, takes place in the absence of inorganic phosphate or at starvation levels of inorganic phosphate in the periplasm and supporting culture medium, resulting in an increase or an extension of product accumulation.

E. Detecting Expression

Gene expression may be measured in a sample directly, for example, by conventional northern blotting to quantitate the transcription of mRNA (Thomas, *Proc. Natl. Acad. Sci. USA*, 77: 5201-5205 (1980)), dot blotting (RNA analysis), or in situ hybridization, using an appropriately labeled probe, based on the sequences that encode the polypeptide. Various labels may be employed, most commonly radioisotopes, particularly $^{32}$P. However, other techniques may also be employed, such as using biotin-modified nucleotides for introduction into a polynucleotide. The biotin then serves as the site for binding to avidin or antibodies, which may be labeled with a wide variety of labels, such as radionuclides, fluorescers, enzymes, or the like. Alternatively, assays or gels may be employed for detection of protein.

For secretion of an expressed gene product, the host cell is cultured under conditions sufficient for secretion of the gene product. Such conditions include, e.g., temperature, nutrient, and cell density conditions that permit secretion by the cell. Moreover, such conditions are those under which the cell can perform the basic cellular functions of transcription, translation, and passage of proteins from one cellular compartment to another, as are known to those skilled in the art.

F. Purification of Polypeptides

The following procedures, individually or in combination, are exemplary of suitable purification procedures, with the specific method(s) used being dependent on the type of polypeptide: fractionation on immunoaffinity or ion-exchange columns; ethanol precipitation; reversed-phase HPLC; hydrophobic-interaction chromatography; chromatography on silica; chromatography on an ion-exchange resin such as S-SEPHAROSE™ and DEAE; chromatofocusing; SDS-PAGE; ammonium-sulfate precipitation; and gel filtration using, for example, SEPHADEX™ G-75 medium.

The monoclonal antibodies may be suitably separated from the culture medium by conventional antibody purification procedures such as, for example, protein A-SEPHAROSE™ medium, hydroxyapatite chromatography, gel electrophoresis, dialysis, or affinity chromatography.

The invention will be more fully understood by reference to the following examples. They should not, however, be construed as limiting the scope of the invention. All literature and patent citations herein are incorporated by reference.

EXAMPLE 1

Feeding of G3P to Shake Flask Culture for the Production of Llama Antibody Fragment (Heavy Chain) and Apo2L Background The inclusion of 200 mM G3P (final concentration) in either low-phosphate (CRAP) or high-phosphate culture medium (THCD) was compared to the respective control addition (water) for the expression of a heterologous protein in shake-flask culture. In the first part of this Example, the target heterologous protein is a 13 kD llama anti-HCG camelid monobody. Camelid antibodies have been previously shown to have 2 species, a classic IgG molecule consisting of two heavy plus two light chains and a heavy-chain IgG molecule lacking a light chain referred to as monobody. The camelid monobody was expressed by BL21, an *E. coli* B strain, using a tac promoter in either a low-phosphate (CRAP)- or a high-phosphate (THCD)-rich media. The malE binding protein signal sequence preceding the antibody-fragment-encoding sequence directed the secretion of the expression protein into the periplasm of the host. In the second part of this Example, a T7 promoter was used to regulate the expression of Apo2 ligand in HMS174, an *E. coli* K12 strain, in G3P-supplemented and unsupplemented CRAP medium. Production of heterologous protein in both experiments was induced with the addition of IPTG upon reaching the desired cell density.

Materials & Methods:

pCB36624_86.RIG Plasmid Construction:

pCB36624_86.RIG_ was constructed by modifying vector pL1602 (Sidhu et al., *J. Mol. Biol.*, 296:487-495 (2000)). Vector pS1602, which has pTac promoter sequence and malE secretion signal sequence, contained a sequence of human growth hormone fused to the C-terminal domain of the gene-3 minor coat protein (p3) of phage mu. The sequence encoding hGH was removed and the resulting vector sequence served as the vector backbone for the insertion of a synthetic DNA fragment encoding the llama anti-HCG antibody (Spinelli et al., *Nat. Struct. Biol.* 3(9): 752-757 (1996)). The resulting phagemid (pCB36624) encoded the fusion product under the control of the IPTG-inducible $P_{tac}$ promoter (Amman and Brosius, *Gene*, 40: 183-190 (1985)). The expressed polypeptide included the maltose-binding protein signal peptide, followed by the anti-HCG coding region, followed by a FLAG epitope tag, followed by a Gly/Ser-rich linker peptide containing a suppressible stop codon, followed by P3C (the C-terminal domain of the phage coat protein).

Phage-displayed libraries were constructed using the method of Sidhu et al., *J. Mol. Biol.*, 296: 487-495 (2000) with appropriately designed "stop template" phagemids. For library NNS17, a derivative of pCB36624 that contained TAA stop codons in place of codons 93, 94, 100 and 101 was used as the template for the Kunkel mutagenesis method (Kunkel et al., *Methods Enzymol.*, 154: 367-382 (1987)), with mutagenic oligonucleotide NNS17 designed to simultaneously repair the stop codons and introduce 17 NNK degenerate codons between the codons encoding Gly95 and Trp103.

NNS17:

```
                                          (SEQ ID NO: 3)
GCC GTC TAT ACT TGT GGT GCT GGT NNS NNS NNS NNS
NNS NNS NNS NNS NNS NNS NNS NNS NNS NNS NNS NNS
NNS TGG GGT CAG GGT
```

Like all monobodies, the llama anti-HCG is a Vh3 family member and as such is recognized by Protein A. The Protein A binding interaction was used as a surrogate for CDR3-mediated stability. The resulting phage libraries were sorted by multiple rounds against Protein A as readout of scaffold stability and expression. The sorted libraries were analyzed for selection bias in the distribution of amino acids in the NNS library. Scaffold RIG, as named by the sequence at positions 96, 97 and 98, turned out to be the most dominant clone based on the sequenced residues. The 17-amino-acid-long CDR3 sequence for Scaffold RIG was determined to be RIGRS-VFNLRRESWVTW (SEQ ID NO:4). The phagemid with Scaffold RIG is renamed pCB36624_86.RIG, with the DNA sequence:

```
                                          (SEQ ID NO: 5)
5'-GATGTTCAGT TGCAGGAATC AGGCGGTGGC TTGGTACAGG

CCGGAGGTTC GTTGCGTTTG TCCTGTGCTG CCTCGGGTGC

TACTGGTTCT ACTTATGATA TGGGCTGGTT TCGTCAGGCT

CCGGGTAAAG AACGTGAATC GGTTGCCGCC ATTAACTGGG

GGTCGGCTGG GACTTACTAT GCTTCGTCCG TCCGTGGTCG

TTTTACTATT TCACGTGATA ATGCCAAAAA AACTGTCTAT

TTGCAGATGA ATTCATTGAA ACCAGAAGAT ACTGCCGTCT

ATACTTGTGG TGCTGGTAGG ATCGGCCGGT CGGTCTTCAA

CTTGAGGAGG GAGAGCTGGG TCACGTGGTG GGGTCAGGGT

ACCCAGGTCA CTGTCTCCTC TGCCGGTGGT ATGGATTATA

AAGATGATGA TGATAAA-3'
``` pet19b.nohis Plasmid Construction

Using standard molecular biology techniques, Apo2L codons 114-281 were amplified by polymerase chain reaction from a full-length Apo2L clone isolated from human placental cDNA. Additional nucleotides containing restriction sites to facilitate cloning are added to the 5' and 3' sequences, respectively. The 5' oligonucleotide primer has the sequence:

```
                                          (SEQ ID NO: 6)
5' GCTTGCTACATATGGTGAGAGAAAGAGGTCCTCAGAGA 3'
``` containing the underlined Nde I restriction site. The 3' oligonucleotide primer has the sequence:

```
                                          (SEQ ID NO: 7)
5' CTTGAATAGGATCCCTATTAGCCAACTAAAAAGGCCCCAAAA AA

ACTGGC 3'
``` containing the underlined BamH I restriction site. The resulting fragment was subcloned using the restriction sites Nde I to BamH I into a modified baculovirus expression vector pVL1392 (Pharmingen) in frame and downstream of a sequence containing a His10 tag and an enterokinase cleavage site (Pitti et al., *J. Biol. Chem.*, 271:12687-12690 (1997)). pVL1392-Apo2L was digested with Nde I and BamH I and the Nde I-to-BamH I fragment generated was subcloned into pET-19b (Novagen), also digested with Nde I and BamH I. The resultant plasmid was named pet19b.nohis.

Bacterial Strains:

Competent cells of BL21 (Stratagene) and HMS174 (Merck) were transformed with pCB36624_86.RIG and pet19b.nohis, respectively, using standard procedures. Transformants were picked after growth on an LB plate containing 50 µg/mL carbenicillin (LB+CARB50™ carbenicillin), streak-purified, and grown in LB broth with 50 µg/mL CARB50™ carbenicillin in a 30° C. incubator. pCB36624_86.RIG conferred carbenicillin resistance to the production host BL21/pCB36624_86.RIG and pet19b.nohis to HMS174/pet19b.nohis, allowing the transformed hosts to grow in the presence of the antibiotic.

Fermentation Medium:

Both low-phosphate (CRAP) culture medium and high-phosphate (THCD) culture medium were used for the evaluation of production of llama antibody fragment and Apo2 ligand. The media composition (with the quantities of each component utilized per liter of initial medium) is listed below:

| Ingredient | Low-PO$_4$ Medium Quantity/L | High-PO$_4$ Medium Quantity/L |
|---|---|---|
| Glucose | 5.5 g | 5.5 g |
| Ammonium Sulfate | 3.57 g | 3.57 g |
| Na$_2$HPO$_4$ | — | 1.86 g |
| NaH$_2$PO$_4$—H$_2$O | — | 0.93 g |
| Sodium Citrate, Dihydrate | 0.71 g | 0.71 g |
| Potassium Chloride | 1.07 g | 1.07 g |
| 1M Magnesium Sulfate | 7 ml | 7 ml |
| Hycase SF | 5.36 g | — |
| Yeast Extract | 5.36 g | 5.36 g |
| Casamino Acids | — | 5.36 g |
| 1M MOPS, ph 7.3 | 110 ml | 110 ml |
| KOH for pH adjustment to pH 7.3 | as needed | as needed |

To prepare 200 mM of G3P-supplemented medium, 5 ml of 1 M DL-alpha-glycerophosphate (G3P) (Sigma Chem. Co.) was added to 20 ml of low-PO$_4$ medium with 50 µg/ml of carbenicillin (low-PO$_4$ medium+CARB50™ carbenicillin) or high-PO$_4$ medium with 50 µg/ml of carbencillin (high-PO$_4$ medium+CARB50™ carbenicillin) prior to inoculation. For the unsupplemented (control) medium, 5 ml of water was used in place of G3P.

Shake-Flask Fermentation:

Shake-flask fermentation was conducted in a 125-ml baffled flask containing 25 ml of control or G3P-supplemented medium. An overnight culture of BL21/pCB36624_86.RIG or HMS174/pet19b.nohis grown in LB+CARB50™ carbenicillin was back-diluted at approx. 1:100 for inoculation into the control or G3P-supplemented media. Cultures were incubated at 30° C. on a shaker at 250 RPM and product expression was induced by the addition of 1 mM of IPTG when cell density reached approximately 50-60% of the potential cell growth supported by the medium. Cell pellets from 1 ml of broth culture, taken just before the addition of the inducer and at approximately 24 hrs post-inoculation, were prepared and stored at –20° C.

Llama Antibody Fragment Accumulation Analyzed by PAGE and Densitometry:

Frozen (–20° C.) cell pellet prepared from 1 ml of culture sample was thawed and resuspended in sufficient quantity of 10 mM TRIS, pH 7.6+1 mM EDTA, pH 8.0 (TE) to bring the cell suspension to 1 OD/25 µl concentration. 25 µl of the TE-cell suspension was mixed with 25 µl of 2× sample buffer containing beta-mercaptoethanol. The mixture was heated at >95° C. for 5 mins before 10 µl (equivalent to 0.2 OD) was loaded per well onto NU-PAGE™ precasted 10% Bis-Tris gel (Novex). Electrophoresis was performed in MES buffer (2-(N-morpholino) ethanesulphonic acid in deionised water adjusted to the appropriate pH, such as with 1 N NaOH). The resolved gel was stained with COOMASSIE BLUE R250™ stain and then destained. The band intensity of the 13-kD antibody fragment was determined using Kodak DIGITAL SCIENCE 1D™ imaging software after scanning the wet gel with the Kodak imaging system.

Apo2 Ligand Accumulation Analyzed by Reversed-Phase HPLC:

Frozen (–20° C.) cell pellet prepared from 1 ml of culture sample was resuspended in sufficient quantity of TE buffer to bring the cell suspension to 1 OD/25 µl concentration. 20 µl of the cell suspension was mixed into 480 µl of 6 M guanidine HCl, pH 9.0+100 mM dithiothreitol (DTT), and was allowed to incubate at room temperature for an hour before being centrifuged at 13,000 rpm for 15 mins to recover the supernatant/extract. The extract was filtered through a MILLIPORE™ spin-filter before 20 µl was loaded onto an HPLC column (PerSeptive Biosystems POROS® R1/10 medium) for reverse-phase chromatography. The HPLC separation was conducted at 80° C. with the mobile phases flowing at 1.0 ml/min and employed a gradient of 28% to 35% of acetonitrile with 0.1% TFA over 20 minutes for the resolution of the Apo2L away from the contaminating proteins. Peak detection was at 280 nm wavelength. The amount of monomer present in samples was calculated using an average response factor (mAU/µg) derived from the area under the peak associated with 5-20 µg of purified standards analyzed by the same method.

Results:

FIG. 1 shows that the antibody is expressed to higher levels in both high-PO$_4$ (THCD) and low-PO$_4$ (CRAP) medium supplemented with 200 mM G3P versus the control.

FIG. 2 shows that the Apo2L protein is expressed to higher levels in low-PO$_4$ (CRAP) medium supplemented with 200 mM G3P versus the control.

EXAMPLE 2

Feeding of G3P to 10-L Fermentor Culture of Wild-Type or (ΔglpT phoA– ugp+) Host for Production of IGF-I Regulated by Alkaline Phosphatase Promoter Materials & Methods:

pBKIGF-2B Plasmid for Expression of IGF-I:

The plasmid pBKIGF-2, used for the expression of IGF-I herein, was constructed as detailed in U.S. Pat. No. 5,342,763. This plasmid was constructed from a basic backbone of pBR322. The transcriptional and translational sequences required for expression of the IGF-I gene in *E. coli* are provided by the alkaline phosphatase promoter and the trp Shine-Dalgarno sequences. The lambda t$_o$ transcriptional terminator is situated adjacent to the IGF-I termination codon. Secretion of the protein from the cytoplasm is directed by the lamB signal sequence. The majority of rhIGF-I is found in the cell periplasmic space. Plasmid pBKIGF-2B confers tetracycline resistance upon the transformed host.

Bacterial Strains and Growth Conditions:

The hosts used in the IGF-I fermentation are derivatives of *E. coli* W3110 (Bachmann, *Cellular and Molecular Biology*, vol. 2 (Washington, D.C.: American Society for Microbiology, 1987), pp. 1190-1219). Experiments concerning a host with wild-type glpT were carried out with strain 43E7 (*E. coli* W3110 fhuA(tonA) Δ(argF-lac) ptr3 degP41 ΔompTΔ(nmpc-fepE) ilvG+ phoA), and experiments concerning a host with a ΔglpT mutation were carried out with strain 43F6 (*E. coli* W3110 fhuA(tonA) Δ(argF-lac) ptr3 degP41 ΔompTΔ(nmpc-fepE) ilvG+ phoA ΔglpT). Competent cells of 43E7 or 43F6 were transformed with pBKIGF-2B using standard procedures. Transformants were picked after growth on an LB plate containing 20 µg/mL tetracycline (LB+TET20™ tetracycline), streak-purified, and grown in LB broth with 20 µg/mL TET20™ tetracycline in a 37° C. shaker/ incubator before being tested in the fermentor. pBKIGF-2B confers tetracycline resistance to the production host and allows the transformed host to grow in the presence of the antibiotic.

10-L Fermentation Process:

The fermentation medium composition and run protocol used for the expression of IGF-I were somewhat similar to those used in the IGF-I process described in U.S. Pat. No. 5,342,763. Briefly, a shake-flask seed culture of 43E7/pBKIGF-2 or 43F6/pBKIGF-2 was used to inoculate the rich production medium. The composition of the medium (with the quantities of each component utilized per liter of initial medium) is described below:

| Ingredient | Quantity/L |
| --- | --- |
| Glucose* | 200-500 g |
| Ammonium Sulfate | 2-10 g |
| Sodium Phosphate, Monobasic Dihydrate | 1-5 g |
| Potassium Phosphate, Dibasic | 1-5 g |
| Sodium Citrate, Dihydrate | 0.5-5 g |
| Potassium Chloride | 0.5-5 g |
| Magnesium Sulfate, Heptahydrate | 0.5-5 g |
| PLURONIC ™ Polyol, L61 | 0.1-5 mL |
| Ferric Chloride, Heptahydrate | 10-100 mg |
| Zinc Sulfate, Heptahydrate | 0.1-10 mg |
| Cobalt Chloride, Hexahydrate | 0.1-10 mg |
| Sodium Molybdate, Dihydrate | 0.1-10 mg |
| Cupric Sulfate, Pentahydrate | 0.1-10 mg |
| Boric Acid | 0.1-10 mg |
| Manganese Sulfate, Monohydrate | 0.1-10 mg |
| Hydrochloric Acid | 10-100 mg |
| Tetracycline | 4-30 mg |
| Yeast Extract* | 5-25 g |
| NZ Amine AS* | 5-25 g |
| Methionine* | 0-5 g |
| Ammonium Hydroxide | as required to control pH |
| Sulfuric Acid | as required to control pH |

*A portion of the glucose, yeast extract, methionine, and NZ Amine AS is added to the medium initially, with the remainder being fed throughout the fermentation.

The 10-liter fermentation was a fed-batch process with fermentation parameters set as follows:

| | |
| --- | --- |
| Agitation: | 1000 RPM |
| Aeration: | 10.0 slpm |
| pH control: | 7.3 |
| Temp.: | 37° C. |
| Back pressure: | 0.3 bar |
| Glucose feed: | computer-controlled using an algorithm to maintain the dissolved oxygen concentration ($DO_2$) at 30% of air saturation after the $DO_2$ drops to 30%. |
| Complex nitrogen feed: | constant feed rate of 0.2 mL/min beginning when $OD_{550}$ reaches 40 and maintained for the remaining time of the run |
| Run Duration: | 40 to 50 hours |

In experiments involving glycerol-3-phosphate (G3P) feeding, the appropriate amount of 1 M G3P stock solution was spiked into the complex nitrogen feed and the subsequent supplemented feed feed-rate increased to deliver the desired amount of complex nitrogen plus G3P to the culture.

The impact of the ΔglpT mutation with or without the G3P feeding was assessed by the difference in the IGF-I accumulation. The total amount of IGF-I in a sample solubilized in 6M guanidine+100 mM DTT was measured by a reversed-phase HPLC method as described in U.S. Pat. No. 6,559,122.

Results:

FIG. 3 shows that with the wild-type host (43E7) and AP promoter and continuously fed glucose, the amount of secreted IGF-I was distinctly higher when G3P was fed to the medium than when G3P was not added.

FIG. 4 shows that with the ΔglpT host (43F6) and AP promoter, the amount of secreted IGF-I was distinctly higher when G3P was fed to the culture at 1.18 or 3.28 mmoles/hour, per approximately 8 liters, than when G3P was not added, but was not higher when 8.22 mmoles/hour, per approximately 8 liters, of G3P was fed. The optimum feed rate will be readily determined by one skilled in the art based on the product, type of organophosphate, etc. Under the conditions of the fermentation process described, culturing in a 10-liter fermentor to produce IGF-I, there is an optimal G3P feed rate, per approximately 8-10 liters, in the preferred range of about 1-7 mmoles/hour, more preferably about 1-6 mmoles/hour, still more preferably about 2-6 mmoles/hour, yet more preferably about 2-5 mmoles/hour, and most preferably about 3-4 mmoles/hour. Not only does this range of feed rates increase the amount of product over control, but also it extends the duration of production relative to the control.

EXAMPLE 3

Feeding of Glycero-3-Phosphate to Improve Apo2 Ligand Accumulation in the 10-L Process Background on Apo2 Ligand Apoptosis-inducing ligand 2 (Apo2L) (Pitti et al., *J. Biol. Chem.*, 271: 12687-12690 (1996)), also known as tumor necrosis factor-related apoptosis inducing ligand (TRAIL) (Wiley et al., *Immunity*, 3: 673-682 (1995)), is a type II membrane protein and a member of the TNF family of ligands. Apo2L/TRAIL triggers apoptosis in a wide variety of cancer cells, but not in most normal cells, through binding to its cognate death receptors (WO 99/00423; Ashkenazi, *FASEB J.*, 13: (7) A1336 (Apr. 23, 1999); Ashkenazi, *Nature Reviews—Cancer*, 2: 420-430 (2002)). A soluble fragment of the extracellular domain of Apo2 ligand, corresponding to amino acid residues 114-281 (from here on referred to as Apo2L/TRAIL), is currently under investigation for potential clinical studies and has been successfully expressed in *E. coli*.

General Description of the Fermentation Process:

The expression vector encodes for the use of the alkaline phosphatase (AP) promoter to regulate the production of the approximately 19.5-kDa polypeptide. The expressed nascent polypeptides, upon release from the ribosomes, fold into monomers in the cytoplasm and further associate to become the biologically active homotrimer. During fermentation, the process parameters are set such that cellular activities are conducted at peak oxygen uptake rates of approximately 3.0 mmoles/L-min. After broth harvest, the cytoplasmically trapped heterologous protein is released by mechanical cell disruption into the cell lysate from which it may be recovered.

Materials and Methods:

pAPApo2-P2RU Plasmid Construction: pAPApo2-P2RU is described in WO 01/00832 published Jan. 4, 2001. Briefly, this plasmid, the construct of which is shown in FIG. 5, encodes the co-expression of Apo-2L (amino acid residues 114-281) and the rare-codon tRNA's encoded by pro2 and argU, which co-expression is regulated by the alkaline phosphatase promoter. The pBR322-based plasmid (Sutcliffe, *Cold Spring Harbor Symp. Quant. Biol.*, 43:77-90 (1978)) pAPApo2-P2RU was used to produce the Apo-2L in *E. coli*. The transcriptional and translational sequences required for the expression of Apo-2L are provided by the alkaline phosphatase promoter and the trp Shine-Dalgarno sequence, as described for the plasmid phGH1 (Chang et al., *Gene*, 55:189-196 (1987)). The coding sequence for Apo-2L (from 114-281) is located downstream of the promoter and Shine-Dalgarno sequences and is preceded by an initiation methionine. The coding sequence includes nucleotides (shown in FIG. 6) encoding residues 114-281 of Apo-2L (FIG. 6-SEQ ID NOS:1 and 2, respectively, for nucleotide and amino acid sequences) except that the codon encoding residue Pro119 is changed to "CCG" instead of "CCT" in order to eliminate potential secondary structure. The sequence encoding the lambda $t_o$ transcriptional terminator (Scholtissek et al., *Nucleic Acids Res.*, 15: 3185 (1987)) follows the Apo-2L coding sequence.

Additionally, this plasmid also includes sequences for the expression of the tRNA's pro2 (Komine et al., *J. Mol. Biol.*, 212:579-598 (1990)) and argU/dnaY (Garcia et al., *Cell*, 45:453-459 (1986)). These genes were cloned by PCR from *E. coli* W3110 and placed downstream of the lambda $t_o$ transcriptional-terminator sequence. This plasmid confers both tetracycline and ampicillin resistance upon the production host.

Bacterial Strains and Growth Conditions:

Strain 43E7 (*E. coli* W3110 fhuA(tonA) phoAΔ(argF-lac) ptr3 degP ompT ilvG+)) was used as the wild-type production host for comparison to 43F6, the glpT-mutated host for the expression of Apo2 ligand and the rare codon tRNA's. Competent cells of 43E7 or 43F6 were prepared and transformed with pAPApo2-P2RU using standard procedures. Transformants were picked from LB plates containing 20 μg/ml tetracycline (LB+Tet20), streak-purified, and grown in LB broth with 20 μg/ml tetracycline in a 30° C. shaker/incubator before being stored in DMSO at –80° C.

Fermentation Process for Apo2L Production:

A shake-flask inoculum was prepared by inoculating sterile LB medium containing 4-6 mM sodium phosphate with a freshly thawed stock culture vial. Appropriate antibiotics were included in the medium to provide selective pressure to ensure retention of the plasmid. Flask cultures were incubated with shaking at about 30° C. (28° C.-32° C.) for 14-18 hours. This culture was then used to inoculate the production fermentation vessel. The inoculation volume was between 0.1% and 10% of the initial volume of medium.

Production of Apo2L was carried out in the production medium given in Table 1 to achieve a final culture volume of approximately 10 liters. The fermentation process was conducted at about 30° C. (28-32° C.) and pH controlled at approximately 7.0 (6.5-7.5). The aeration rate and the agitation rate were set to provide adequate transfer of oxygen to the culture. Just prior to depletion of the batched phosphate (at approximately 75-85 OD), a DL-alpha-glycerophosphate feed (vendor product specification shows product purity at 80-90%, with beta-glycerophosphate listed as the main impurity) was initiated and fed at the desired feed rate. Throughout the fermentation process, the cell culture was fed glucose as the primary carbon source based on a computer algorithm while ensuring aerobic conditions.

Two batch additions of approximately 50-150 μM (final concentration) $ZnSO_4$ were made during the fermentation process, one just prior to the induction of product expression, the other at approximately the mid-point of the production period for improved homotrimer assembly. In this example, the additions occurred at a culture optical density of about 80-120 $OD_{550}$ and at about 28 hours post-inoculation.

The fermentation was allowed to proceed for about 34-45 hours before being harvested.

TABLE 1

Production Medium Composition for AP Promoter Expression System

| Ingredient | Quantity/Liter |
|---|---|
| Tetracycline | 4-20 mg |
| Glucose[a] | 10-250 g |
| Ammonium sulfate[a] | 2-8 g |
| Sodium phosphate, monobasic, dihydrate[a] | 1-5 g |
| Potassium phosphate, dibasic[a] | 1-5 g |
| Potassium phosphate, monobasic[a] | 0-5 g |
| Sodium citrate, dihydrate[a] | 0.5-5 g |
| Potassium chloride | 0-5 g |
| Magnesium sulfate, heptahydrate[a] | 1.0-10 g |
| Antifoam | 0-5 ml |
| Ferric chloride, hexahydrate[a] | 20-200 mg |
| Zinc sulfate, heptahydrate[a] | 0.2-20 mg |
| Cobalt chloride, hexahydrate[a] | 0.2-20 mg |
| Sodium molybdate, dihydrate[a] | 0.2-20 mg |
| Cupric sulfate, pentahydrate[a] | 0.2-20 mg |
| Boric acid[a] | 0.2-20 mg |
| Manganese sulfate, monohydrate[a] | 0.2-20 mg |
| Casein hydrolysate[a] | 5-25 g |
| Yeast extract[a] | 5-25 g |

[a]A portion of these ingredients may be fed to the culture during the fermentation. Ammonium hydroxide was added as required to control pH.

Assessment of Soluble Product Accumulation During Fermentation Process by Ion-Exchange HPLC Chromatography Method:

Broth samples were taken over the time course of the fermentation process. Cells from 1 milliliter of broth samples diluted to a cell density of 20 $OD_{550}$ were collected by centrifugation and the resultant cell pellets were stored at –20° C. until analysis. The cell pellets were thawed and resuspended in 0.5 ml of extraction buffer (50 mM HEPES, pH 8.0, 50 mM EDTA and 0.2 mg/ml hen egg-white lysozyme) and mechanically disrupted to release the product from the cytoplasm. Solids were removed from the cell lysates by centrifugation before the clarified lysates were loaded onto an HPLC column (DIONEX PROPAC™ IEX medium) for trimer quantitation. The HPLC assay method resolved the product away from the contaminating *E. coli* proteins by use of a 5%-22% gradient of 1M NaCl in a 25-mM phosphate (pH 7.5) buffer over 25 minutes at a flow rate of 0.5 ml/min.

Assessment of Total Monomeric Apo2L Expression During Fermentation Process by Reversed-Phase HPLC Chromatography:

Fresh culture broth or previously frozen and then thawed samples were used for the quantitation of total monomer production. 20 μl of sample was mixed into 480 μl of 6M guanidine HCl, pH 9.0 with 100 mM DTT and was allowed to incubate at room temperature for an hour before being centrifuged at 13,000 rpm for 15 mins to recover the extract. The extract was filtered through a spin-filter before 20 μl was loaded onto an HPLC column (PerSeptive Biosystems POROS® R1/10 medium) for reverse-phase chromatography. The HPLC separation was conducted at 80° C. with the mobile phases flowing at 1.0 ml/min and employed a gradient of 28% to 35% of acetonitrile with 0.1% TFA over 20 minutes for the resolution of the Apo2L away from the contaminating proteins. Peak detection was at 280-nm wavelength. The amount of monomer present in samples was calculated using an average response factor (mAU/μg) derived from the area under the peak associated with 5-20 μg of purified standards analyzed by the same method.

Results:

FIG. 7 shows an improved specific product titer (referred to as specific titer in μg/OD-ml in the graph) with an optimum G3P feed rate to the ΔglpT host (43F6). All of the G3P-fed runs performed better than the no-feed control. In this example, as the feed rate for an approximately 8-liter culture increased from 6 to 12 mmole/hour, the specific product titer improved, but as the rate increased above 12 mmole/hour to 18 mmole/hour, the specific titer was lower. The optimum feed rate of G3P will be readily determined by one skilled in the art based on the product, type of organophosphate, etc. Under these particular conditions, culturing in a 10-liter fermentor cells for producing this specific product, Apo2L, the preferred feed rate of G3P, per approximately 8-10 liters, is preferably in the range of about 4 to 17 mmole/hour, more preferably about 6 to 16 mmole/hour, still more preferably about 8 to 15 mmole/hour, and most preferably about 10 to 14 mmole/hour.

FIG. 8 shows an improved specific product titer (referred to as specific total accumulation in μg/OD-ml in the graph) feeding G3P over feeding inorganic phosphate to the wild-type glpT host (43E7). While glycerophosphate feeding increased specific total accumulation of Apo2L, feeding inorganic phosphate negatively impacted specific total accumulation compared to the no-feed control. Similar trends would be expected using a lower glycerophosphate feed than was employed. The results here are intended to, and do, show that a high level of expression can be obtained by feeding glycerophosphate to a wild-type glpT host. Further, in this particular experiment, similar to the inorganic phosphate feed case, the culture cell density increased to over 200 OD550 when the glycerophosphate was fed, but not for the no-feed situation.

EXAMPLE 4

Expression of AP Promoter-Driven Apo2L Product During Active Growth Phase

The same plasmid construction, production host strain, medium composition, fermentation process and product assay methods were used as described in Example 3 except for the phosphate batching and the G3P addition. A portion of the inorganic phosphate typically included in the salt batching in a control process was replaced with an equivalent number of moles of G3P, either added immediately after inoculation or a few hours prior to the depletion of the batched inorganic phosphate. In these examples, the added G3P was expected to be the source of phosphate for a significant fraction of the cell growth subsequent to the addition.

Fermentation Process for Apo2L Production During Active Growth Phase:

The inoculum preparation protocol was the same as that described in Example 3. Production of Apo2L was carried out in the production medium given in Table 1 except that either 75% or 50% of the phosphate salts was eliminated from the initial batching and replaced with an equivalent number of moles of G3P added back as a batch addition post inoculation. The fermentation was conducted at about 30° C. (28-32° C.) and pH was controlled at approximately 7.0 (6.5-7.5) as per standard protocol. The aeration rate and the agitation rate were as described in Example 3. For the case where 50% of the inorganic phosphate was replaced with G3P, the inorganic phosphate was batched in prior to medium sterilization while the glycerol-3-phosphate replacement was made approximately 1-2 hours before the batched phosphate was expected to run out (at approximately 30-40 $OD_{550}$). For the case where 75% of the inorganic phosphate was replaced with G3P, both the inorganic phosphate and the G3P were added immediately after the inoculation of the fermentor. Throughout the fermentation process, the cell culture was fed glucose as the primary carbon source based on a computer algorithm while ensuring aerobic conditions. In additions were made during the fermentation process as described in the earlier section. The fermentation was allowed to proceed for about 34-45 hours.

Results:

FIG. 9 shows the induction of heterologous protein expression occurring significantly earlier in the active growth phase when 50%-75% of the $PO_4$ batching was replaced with G3P addition for both the wild-type and glpT-mutated hosts, shifting the specific total accumulation curve to the left of that for the duplicate control cases conducted with the wild-type host with no G3P substitution. This indicates an advantage of this invention in that the product can be obtained earlier during the fermentation process.

While all ratios of P1 to G3P tested herein achieved this advantage regardless of the host type, Table 2 shows that using the 1:1 or 1:3 ratio of P1 to G3P for the glpT-mutated host 43F6 produced the highest volumetric Apo2L productivity rate (an average of about 0.34 versus an average of about 0.24 mg/ml-hr for the control host). Further, using either ratio and the wild-type or mutated host achieved the peak specific accumulation (in μg/OD-ml) earlier (22 to 26 hours versus 28 to 30 hours). This shows that in certain preferred embodiments, the invention can achieve similar, if not higher, amounts of monomeric Apo2L in approximately 10% to 25% less fermentation time than otherwise to improve process productivity significantly.

TABLE 2

Effect of Replacing Inorganic Phosphate Initial Batching with Glycerophosphate Addition During the First 30 Hours of Fermentation

| Experiment | Volumetric Productivity Rate (mg/ml-hr) | Time to Peak Specific Accum. (μg/OD-ml) | Peak Total monomeric Apo2L Yield (g/L) |
|---|---|---|---|
| Control (43E7) | 0.27 | 28 | 2.9 |
| Control (43E7) | 0.21 | 30 | 2.8 |
| Pi/G3P @ 1:1 (43F6) (50% replacement) | 0.34 | 22.5 | 3.3 |
| Pi/G3P @ 1:1 (43E7) (50% replacement) | 0.25 | 22 | 2.0 |
| Pi/G3P @ 1:3 (43F6) (75% replacement) | 0.34 | 26.0 | 3.0 |

EXAMPLE 5

Expression of AP Promoter-Driven Apo2L Product Using a 50/50 Mixture of Alpha- and Beta-Glycerophosphate A procedure similar to that described in Example 3 was followed except that a cheaper grade of approximately 50:50 mix of alpha- and beta-glycerophosphate was employed instead of G3P as the feed using strain 61G1 (glpT mutant host).

Results

FIG. 10 shows that similar yield improvement over the no-feed control was obtained using the mixture or the higher grade G3P material. Use of the alpha/beta mixture would lessen the cost of raw material without compromising the production results.

What is claimed is:

1. A process for producing Apo2L polypeptide recombinantly comprising:
   (a) culturing *Escherichia coli* (*E. coli*) cells comprising a heterologous nucleic acid encoding the Apo2L in a culture medium while feeding to the culture medium a transportable organophosphate, such that the nucleic acid is expressed, and
   (b) recovering the Apo2L polypeptide from the cells.

2. The process of claim 1 wherein the organophosphate is a glycerophosphate.

3. The process of claim 2 wherein the glycerophosphate is an alpha-glycerophosphate or beta-glycerophosphate, or a mixture thereof.

4. The process of claim 3 wherein the glycerophosphate is a mixture of glycerol-2-phosphate and glycerol-3-phosphate or is glycerol-3-phosphate.

5. The process of claim 1 wherein the culturing takes place in a shake flask or fermentor.

6. The process of claim 1 wherein the polypeptide is recovered from the cytoplasm, periplasm or culture medium of the cells.

7. The process of claim 1 wherein expression of the nucleic acid is regulated by an inducible promoter.

8. The process of claim 7 wherein the inducible promoter is the alkaline phosphatase promoter.

9. The process of claim 7 wherein the inducible promoter is the tac promoter.

10. The process of claim 7 wherein the inducible promoter is the T7 promoter.

11. The process of claim 7 wherein expression of the nucleic acid begins while in the active growth phase of the culturing step.

12. The process of claim 1 wherein the *E. coli* is deficient in chromosomal phoA.

13. The process of claim 1 wherein the *E. coli* is wild type with respect to chromosomal glpT.

14. The process of claim 1 wherein the *E. coli* is deficient in chromosomal glpT.

15. The process of claim 1 wherein the *E. coli* is deficient in chromosomal phoA and glpT.

16. The process of claim 15 wherein the *E. coli* is not deficient in chromosomal ugp.

17. The process of claim 1 wherein the feed rate of the organophosphate is from about 4 to 17 mmoles/hour per about 8-10 liters and the culturing takes place in a 10-liter fermentor.

18. The process of claim 17 wherein the feed rate is from about 6 to 16 mmole/hour per about 8-10 liters.

19. The process of claim 18 wherein the feed rate is from about 8 to 15 mmole/hour per about 8-10 liters.

20. The process of claim 19 wherein the feed rate is from about 10 to 14 mmole/hour per about 8-10 liters.

21. The process of claim 1, wherein an inorganic phosphate is present in the culture medium during the culturing step.

22. The process of claim 21, wherein the ratio of inorganic phosphate to organic phosphate ranges from about 1:10 to 1:0.25 during the culturing step.

23. The process of claim 22 wherein the ratio is about 1:3 to 1:0.5.

24. The process of claim 23 wherein the ratio is about 1:1.

* * * * *

SEQUENCE LISTING

<160> NUMBER OF SEQ ID NOS: 7

<210> SEQ ID NO 1
<211> LENGTH: 1042
<212> TYPE: DNA
<213> ORGANISM: Homo sapiens
<220> FEATURE:
<221> NAME/KEY: Unsure
<222> LOCATION: 447
<223> OTHER INFORMATION: Unknown base

<400> SEQUENCE: 1

```
tttcctcact gactataaaa gaatagagaa ggaagggctt cagtgaccgg            50
ctgcctggct gacttacagc agtcagactc tgacaggatc atggctatga           100
tggaggtcca ggggggaccc agcctgggac agacctgcgt gctgatcgtg           150
atcttcacag tgctcctgca gtctctctgt gtggctgtaa cttacgtgta           200
ctttaccaac gagctgaagc agatgcagga caagtactcc aaaagtggca           250
ttgcttgttt cttaaaagaa gatgacagtt attgggaccc caatgacgaa           300
gagagtatga acagcccctg ctggcaagtc aagtggcaac tccgtcagct           350
cgttagaaag atgattttga gaacctctga ggaaaccatt tctacagttc           400
aagaaaagca acaaaatatt tctcccctag tgagagaaag aggtccncag           450
agagtagcag ctcacataac tgggaccaga ggaagaagca acacattgtc           500
ttctccaaac tccaagaatg aaaaggctct gggccgcaaa ataaactcct           550
gggaatcatc aaggagtggg cattcattcc tgagcaactt gcacttgagg           600
aatggtgaac tggtcatcca tgaaaaaggg ttttactaca tctattccca           650
aacatacttt cgatttcagg aggaaataaa agaaaacaca aagaacgaca           700
aacaaatggt ccaatatatt tacaaataca caagttatcc tgaccctata           750
ttgttgatga aaagtgctag aaatagttgt tggtctaaag atgcagaata           800
tggactctat tccatctatc aagggggaat atttgagctt aaggaaaatg           850
acagaatttt tgtttctgta acaaatgagc acttgataga catggaccat           900
gaagccagtt ttttcggggc ctttttagtt ggctaactga cctggaaaga           950
aaaagcaata acctcaaagt gactattcag ttttcaggat gatacactat          1000
gaagatgttt caaaaaatct gaccaaaaca aacaaacaga aa                  1042
```

<210> SEQ ID NO 2
<211> LENGTH: 281
<212> TYPE: PRT
<213> ORGANISM: Homo sapiens

<400> SEQUENCE: 2

```
Met Ala Met Met Glu Val Gln Gly Gly Pro Ser Leu Gly Gln Thr
1               5                   10                  15

Cys Val Leu Ile Val Ile Phe Thr Val Leu Leu Gln Ser Leu Cys
                20                  25                  30

Val Ala Val Thr Tyr Val Tyr Phe Thr Asn Glu Leu Lys Gln Met
                35                  40                  45

Gln Asp Lys Tyr Ser Lys Ser Gly Ile Ala Cys Phe Leu Lys Glu
                50                  55                  60

Asp Asp Ser Tyr Trp Asp Pro Asn Asp Glu Glu Ser Met Asn Ser
                65                  70                  75
```

```
Pro Cys Trp Gln Val Lys Trp Gln Leu Arg Gln Leu Val Arg Lys
                 80                  85                  90

Met Ile Leu Arg Thr Ser Glu Glu Thr Ile Ser Thr Val Gln Glu
             95                 100                 105

Lys Gln Gln Asn Ile Ser Pro Leu Val Arg Glu Arg Gly Pro Gln
            110                 115                 120

Arg Val Ala Ala His Ile Thr Gly Thr Arg Gly Arg Ser Asn Thr
            125                 130                 135

Leu Ser Ser Pro Asn Ser Lys Asn Glu Lys Ala Leu Gly Arg Lys
            140                 145                 150

Ile Asn Ser Trp Glu Ser Ser Arg Ser Gly His Ser Phe Leu Ser
            155                 160                 165

Asn Leu His Leu Arg Asn Gly Glu Leu Val Ile His Gly Lys Gly
            170                 175                 180

Phe Tyr Tyr Ile Tyr Ser Gln Thr Tyr Phe Arg Phe Gln Glu Glu
            185                 190                 195

Ile Lys Glu Asn Thr Lys Asn Asp Lys Gln Met Val Gln Tyr Ile
            200                 205                 210

Tyr Lys Tyr Thr Ser Tyr Pro Asp Pro Ile Leu Leu Met Lys Ser
            215                 220                 225

Ala Arg Asn Ser Cys Trp Ser Lys Asp Ala Glu Tyr Gly Leu Tyr
            230                 235                 240

Ser Ile Tyr Gln Gly Gly Ile Phe Glu Leu Lys Glu Asn Asp Arg
            245                 250                 255

Ile Phe Val Ser Val Thr Asn Glu His Leu Ile Asp Met Asp His
            260                 265                 270

Glu Ala Ser Phe Phe Gly Ala Phe Leu Val Gly
            275                 280

<210> SEQ ID NO 3
<211> LENGTH: 87
<212> TYPE: DNA
<213> ORGANISM: Artificial sequence
<220> FEATURE:
<223> OTHER INFORMATION: Sequence is synthesized
<220> FEATURE:
<221> NAME/KEY: unsure
<222> LOCATION: 25-26, 28-29, 31-32, 34-35, 37-38, 40-41, 43-44, 46-47,
      49-50, 52-53, 55-56, 58-59, 61-62, 64-65, 67-68, 70-71, 73-74
<223> OTHER INFORMATION: unknown base

<400> SEQUENCE: 3
gccgtctata cttgtggtgc tggtnnsnns nnsnnsnnsn nsnnsnnsnn         50
snnsnnsnns nnsnnsnnsn nsnnstgggg tcagggt                       87

<210> SEQ ID NO 4
<211> LENGTH: 17
<212> TYPE: PRT
<213> ORGANISM: Artificial sequence
<220> FEATURE:
<223> OTHER INFORMATION: Sequence is synthesized

<400> SEQUENCE: 4
```

-continued

```
Arg Ile Gly Arg Ser Val Phe Asn Leu Arg Arg Glu Ser Trp Val
1               5                   10                  15
Thr Trp

<210> SEQ ID NO 5
<211> LENGTH: 417
<212> TYPE: DNA
<213> ORGANISM: Artificial sequence
<220> FEATURE:
<223> OTHER INFORMATION: Sequence is synthesized

<400> SEQUENCE: 5
gatgttcagt tgcaggaatc aggcggtggc ttggtacagg ccggaggttc         50
gttgcgtttg tcctgtgctg cctcgggtgc tactggttct acttatgata        100
tgggctggtt tcgtcaggct ccgggtaaag aacgtgaatc ggttgccgcc        150
attaactggg ggtcggctgg gacttactat gcttcgtccg tccgtggtcg        200
ttttactatt tcacgtgata atgccaaaaa aactgtctat ttgcagatga        250
attcattgaa accagaagat actgccgtct atacttgtgg tgctggtagg        300
atcggccggt cggtcttcaa cttgaggagg gagagctggg tcacgtggtg        350
gggtcagggt acccaggtca ctgtctcctc tgccggtggt atggattata        400
aagatgatga tgataaa                                            417

<210> SEQ ID NO 6
<211> LENGTH: 38
<212> TYPE: DNA
<213> ORGANISM: Artificial sequence
<220> FEATURE:
<223> OTHER INFORMATION: Sequence is synthesized

<400> SEQUENCE: 6
gcttgctaca tatggtgaga gaaagaggtc ctcagaga                      38

<210> SEQ ID NO 7
<211> LENGTH: 50
<212> TYPE: DNA
<213> ORGANISM: Artificial sequence
<220> FEATURE:
<223> OTHER INFORMATION: Sequence is synthesized

<400> SEQUENCE: 7
cttgaatagg atccctatta gccaactaaa aaggccccaa aaaaactggc         50
```